_US006399631B1_

(12) United States Patent
Elliott et al.

(10) Patent No.: US 6,399,631 B1
(45) Date of Patent: Jun. 4, 2002

(54) CARBAZOLE NEUROPEPTIDE Y5 ANTAGONISTS

(75) Inventors: Richard L. Elliott, East Lyme; David A. Griffith, Old Saybrook; Marlys Hammond, Salem, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/620,315

(22) Filed: Jul. 21, 2000

Related U.S. Application Data

(60) Provisional application No. 60/145,304, filed on Jul. 23, 1999.

(51) Int. Cl.[7] ............... A61K 31/4375; A61K 31/4439; C07D 215/20
(52) U.S. Cl. .................. 514/314; 514/323; 514/411; 546/175; 546/200; 548/444
(58) Field of Search .................... 548/444; 514/411, 514/314, 323; 546/175, 200

(56) References Cited

U.S. PATENT DOCUMENTS 3,642,817 A * 2/1972 Harrington et al. ......... 260/315
3,896,145 A * 7/1975 Berger et al. ............... 260/315

FOREIGN PATENT DOCUMENTS

| WO | WO0063171 | 10/2000 |
| WO | WO0107409 | 2/2001 |

* cited by examiner

*Primary Examiner*—T. A. Solola
*Assistant Examiner*—Sonya N. Wright
(74) *Attorney, Agent, or Firm*—Peter C. Richardson; Gregg C. Benson; Gabriel L. Kleiman

(57) ABSTRACT

Carbazoles of the formula

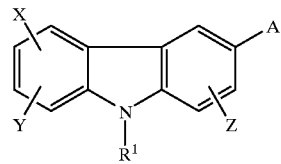

which are effective in treating conditions associated with neuropeptide Y-5 neurotransmission.

25 Claims, No Drawings

CARBAZOLE NEUROPEPTIDE Y5 ANTAGONISTS

This application is filed claiming priority from co-pending Provisional Application No. 60/145,304 filed Jul. 23, 1999.

FIELD OF THE INVENTION

This invention describes a series of carbazole NPY-5 antagonists which bind potently to the NPY-5 receptor and decrease food intake in animal models that are useful in the treatment of obesity, feeding disorders, as well as other neurological diseases related to NPY activity.

BACKGROUND OF THE INVENTION

Neuropeptide Y (NPY), a 36 amino acid peptide neurotransmitter, is a member of the pancreatic polypeptide class of neurotransmitters/neurohormones which has been shown to be present in both the periphery and central nervous system. NPY is one of the most potent orexogenic agents known and has been shown to play a major role in the regulation of food intake in animals, including humans. At least 6 NPY receptor subclasses have been identified and cloned to date, with two of these subclasses, NPY-1 and NPY-5, thought to be the most important receptor subtypes modulating food intake and energy expenditure. Hence, agents capable of blocking NPY binding at these receptor subtype(s) have utility in a number of feeding disorders, including obesity, anorexia nervosa, bulimia nervosa; obesity-related disorders including but not limited to insulin resistance, diabetes, hyperlipidemia, and hypertension, as well other indications for treatment where blockade of NPY activity is beneficial.

A number of NPY-5 receptor antagonist patents have been published. Four patents from Banyu; WO 9827063 [Fukami, Takehiro; Fukuroda, Takahiro; Kanatani, Akio; Ihara, Masaki. Preparation of aminopyrazole derivatives for the treatment of bulimia, obesity, and diabetes. PCT Int. Appl., 38 pp.]; WO 9825907 [Fukami, Takehiro; Fukuroda, Takahiro; Kanatani, Akio; Ihara, Masaki. Preparation of pyrazole derivatives for the treatment of bulimia, obesity, and diabetes. PCT Int. Appl., 63 pp.]; WO 9824768 [Fukami, Takehiro; Fukuroda, Takahiro; Kanatani, Akio; Ihara, Masaki. Preparation of urea moiety-containing pyrazole derivatives as neuropeptide Y antagonists. PCT Int. Appl., 36 pp.]; and WO 9825908 [Fukami, Takehiro; Fukuroda, Takahiro; Kanatani, Akio; Ihara, Masaki. Preparation of novel aminopyrazole derivatives as neuropeptide Y antagonists. PCT Int. Appl., 30 pp.] describe a series of aminopyrazole compounds with potent NPY-5 binding. Novartis has also described a series of Heinrich; Schmidlin, Tibur; Rigollier, Pascal; Yamaguchi, Yasuchika; Tintelnot-Blomley, Marina; Schilling, Walter; Criscione, Leoluca; Stutz, Stefan. Quinazoline derivatives useful as antagonists of NPY receptor subtype Y5. PCT Int. Appl. No. 110 pp.], WO 9720820 [Rueger, Heinrich; Schmidlin, Tibur; Rigollier, Pascal; Yamaguchi, Yasuchika; Tintelnot-Blomley, Marina; Schilling, Walter; Criscione, Leoluca. Quinazoline derivatives useful as antagonists of NPY receptor subtype Y5. PCT Int. Appl. No. 94 pp.], as well as quinazoline-2,4-diazirine NPY-5 antagonists WO 9720822 [Rueger, Heinrich; Schmidlin, Tibur; Rigollier, Pascal; Yamaguchi, Yasuchika; Tintelnot-Blomley, Marina; Schilling, Walter; Criscione, Leoluca. Quinazoline-2,4-diazirines as NPY receptor antagonists. PCT Int. Appl., 154 pp.] and 2-aminoquinazolines WO 9720823 [Rueger, Heinrich; Schmidlin, Tibur; Rigollier, Pascal; Yamaguchi, Yasuchika; Tintelnot-Blomley, Marina; Schilling, Walter; Criscione, Leoluca; Mah, Robert. Preparation of 2-aminoquinazolines as neuropeptide Y subtype Y5 receptor antagonists. PCT Int. Appl., 166 pp.]. Synaptic WO 9746250 [Gerald, Christophe P. G.; Weinshank, Richard L.; Walker, Mary W.; Branchek, Theresa. Methods of modifying feeding behavior, compounds useful in such methods, and DNA encoding a hypothalamic atypical neuropeptide Y/peptide YY receptor. PCT Int. Appl. No. 272 pp] also describes a series of quinazoline NPY-5 antagonists, and WO 9719682 [Islam, Imadul; Dhanoa, Daljit S.; Finn, John M.; Du, Ping; Gluchowski, Charles; Jeon, Yoon T. Preparation of aryl sulfonamide and sulfamide derivatives which bind selectively to the human Y5 receptor. PCT Int. Appl. No. 171 pp.] reports on aryl sulfonamide and sulfamide NPY-5 compounds. Recently, Bayer revealed a series of amide compounds with NPY-5 binding affinity; WO 9835944 [Connell, R. D.; Lease, T. G.; Ladouceur, G. H.; Osterhout, M. H.; Amides as NPY5 Receptor Antagonists. PCT Int. Appl. No. 64 pp.] and WO 9835957 [Connell, R. D.; Lease, T. G.; Ladouceur, G. H.; Osterhout, M. H.; Amide Derivatives as selective Neuropeptide Y Receptor Antagonists. PCT Int. Appl. No. 66 pp.]. Banyu patent WO 9840356 [Preparation and formulation of aminopyridine derivatives as neuropeptide Y receptor antagonists. Fukami, Takehiro; Okamoto, Osamu; Fukuroda, Takahiro; Kanatani, Akio; Ihara, Masaki. (Banyu Pharmaceutical Co., Ltd., Japan). PCT Int. Appl., 78 pp. CODEN: PIXXD2. WO 9840356 A1 980917] covers substituted pyridines as NPY-5 ligands, exemplified by (E)-2-methyl4-pyrrolidino-6-[2-(3-trifluoromethylphenyl)vinyl]pyridine, which in an in vitro test for neuropeptide Y receptor antagonism showed an IC50 of 4.1 nM. However, to date no carbazole NPY-5 receptor antagonists have been described in the scientific or patent literature.

A number of acylated 3-aminocarbazoles are described in the literature. WO 9801417 [Preparation of aryloxyalkylamines, heteroaryloxyalkylamines and their analogs as calcium receptor-active compounds; Sakai, Teruyuki; Takami, Atsuya; Suzuki, Rika, Kirin Beer K. K., Japan; NPS Pharmaceuticals, Inc.; Sakai, Teruyuki; Takami, Atsuya; Suzuki, Rika. PCT Int. Appl., 430 pp.] includes carbazoles of the type shown below.

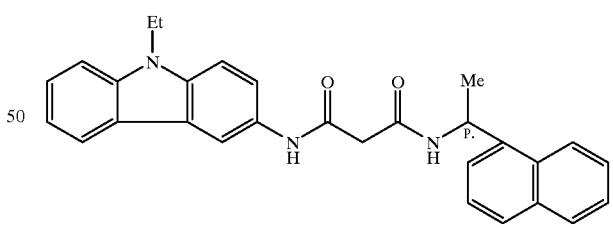

U.S. Pat. No. 4,703,107 A (abandoned) [Preparation and testing of water-soluble polyhydroxyacylpeptide derivatives of drugs and enzyme inhibitors; Monsigny, Michel; Mayer, Roger; Centre National de la Recherche Scientifique, Fr.; U.S., 10 pp. Cont.-in-part of U.S. Ser. No. 610,112] describes a number of amino acid and peptide carbazole amides. Patents GB 2000800 [Pigments for coloring hydrophobic and hydrophilic materials; Dietz, Erwin; Fuchs, Otto; Gutbrod, Robert; Kroh, Adolf; Maikowski, Michael;

Hoechst A.-G., Fed. Rep. Ger.; Brit. UK Pat. Appl., 11 pp.] and JP 54017932 [Pigment compositions; PATENT ASSIGNEE(S): Hoechst A.-G., Fed. Rep. Ger.; SOURCE: Jpn. Kokai Tokkyo Koho, 15 pp.] report on long alkyl chain (C9 or longer) carbazole amides at the 3-position, such as the compound shown below.

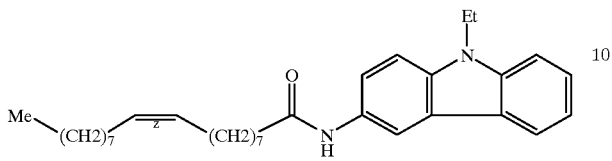

In addition, Japanese patent JP 07053950 [Organic electroluminescent device materials and organic electroluminescent devices with them. Enokida, Toshio; Ogawa, Tadashi. (Toyo Ink Mfg Co, Japan). Jpn. Kokai Tokkyo Koho, 13 pp.] claims compounds of the type below where G1 can be NR9 and G8 is acylamino.

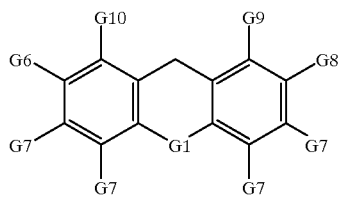

Also, U.S. Pat. No. 4,111,850 [Organic photoconductors; Kwalwasser, William David; AMP Inc., USA; U.S., 12 pp.], claims 3-(acetylamino)-N-ethylcarbazole [6954-68-3] useful as photoconductors, and JP 48091196 [Polyamides containing carbazole rings; Tazuke, Shigeo; Hayashi, Yoshio; Ono, Hisatake; Noguchi, Yasuhiro; Fuji Photo Film Co., Ltd.; Japan. Kokai.] covers carbazole ring-containing polyamides. Also, a Yamanouchi Pharmaceutical Co patent [Ohta, Mitsuaki; Koide, Tokuo; Suzuki, Takeshi; Matsuhisa, Akira; Miyata, Keiji; Ohmori, Junya; Yanagisawa, Isao. Preparation of tetrahydrobenzimidazoles as 5-HT3 receptor antagonists. Eur. Pat. EP 381422] describes a number of tetrahydrobenzimidazoles as 5-HT$_3$ receptor antagonists as exemplified by the formula below.

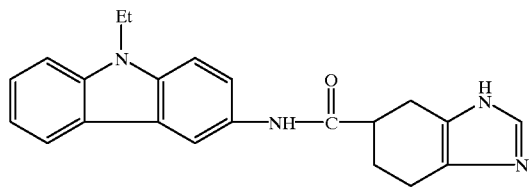

Also, Neurogen patent WO 9806717 [Yuan, Jun; Wasley, Jan William Francis. Preparation of N-[4-(4-phenylpiperazin-1-yl)butyl]-substituted fused indolecarboxamides as dopamine receptor subtype specific ligands] describes a series of 9H-carbazole-3-carboxamide analogs of the general formula below as dopamine receptor ligands.

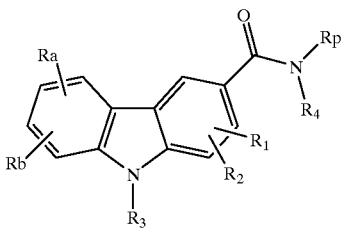

A journal publication by A. Dlugosz [Synthesis and cytotoxicity of the three-membered aromatic pyrimidine derivatives. Dlugosz, Anna. Department of Toxicology, University of Medicine, Wroclaw, 50-417, Pol. Acta Pol. Pharm. (1997), 54(5), 357–362.] reports on 5-pyrimidine carbazole amides shown below.

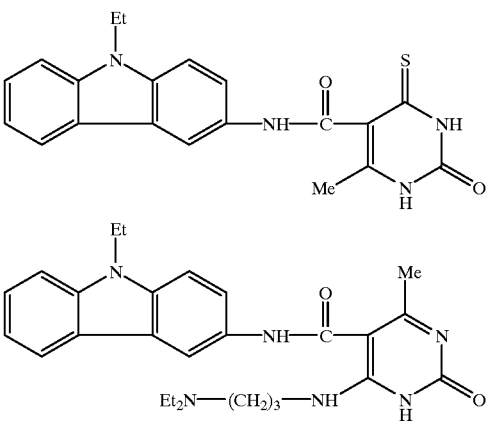

A number of 3-acetamido carbazoles have been described in the chemical literature. The synthesis of 3-acetamido-N-ethyl carbazole has been reported numerous times [e.g. Chakrabarty, Manas; Batabyal, Archana. An expedient synthesis of 5,11-dimethylindolo[3,2-b]carbazole, a potent ligand and the receptor for TCDD. Synth. Commun. (1996), 26(16), 3015–3023]; as has 6-methyl-3-acetamido-N-ethyl carbazole [Perche, J. C.; Saint-Ruf, G.; Buu-Hoi, N. P. Carcinogenic nitrogen compounds. LXXIV. Skraup and Combes-Beyer reactions with 3-aminocarbazoles. New route to pyrido[3,2-b]carbazoles. J. Chem. Soc., Perkin Trans. 1 (1972), Issue 2, 260–2.], 3-benzoylamido-N-ethyl carbazole [Bimolecular reduction of 3-nitro-9-ethylcarbazole. Kyziol, Janusz B.; Wozniak, Waldemar P. Pedagog. Univ., Opole, 45052, Pol. Pol. J. Chem. (1981), 55(4), 937–40.] and N,N'-(9-ethyl-9H-carbazole-3,6-diyl) bis-Acetamide [Dyadyusha, G. G.; Kachkovskii, A. D.; Kolesnikov, A. M.; Mikhailenko, F. A. Interactions of the chromophores of bis(carbocyanines), bis(thiazoloacridine) derivatives, and bis(thiazolocarbazole). Zh. Org. Khim. (1988), 24(1), 185–92.] and N-ethyl-N-(9-ethyl-9H-carbazol-3-yl)-Acetamide,[Flo, Camran; Pindur, Ulf. Reactions of electron-rich heterocycles with orthocarboxylic acid derivatives. 10. Formylation and alkylation of carbazoles with ambient dialkoxycarbenium tetrafluoroborates. Liebigs Ann. Chem. (1987), Issue 6, 509–13.] Another paper [Domanski, Andrzej; Kyziol, Janusz B. Syntheses of bis-basic substituted 9-ethylcarbazoles. Pol. J. Chem. (1985), 59(5–6), 613–20.] describes compounds of the formula shown below [where R=H, Me, Et; R1=CO2R2 (R2=Et, Bu, hexyl, $CH_2CH_2NMe_2$, $CH_2CH_2CH_2NMe_2$, etc.), $CONMe_2$, $CONEt_2$, $CH_2NMe_2$, $CH_2NEt_2$, $NHCO_2CH_2Ph$, $NHCO_2Et$]

which were prepared. and tested for antiviral activity against encephalomyocarditis virus infection in mice.

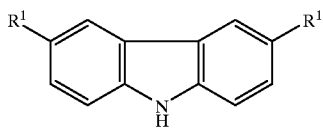

In addition, the preparation of N-(4,6-diamino-9-ethyl-9H-carbazol-3-yl)-acetamide [Lancelot, Jean Charles; Rault, Sylvain; Robba, Max. Imidazo[4,5-c]carbazoles: synthesis and nuclear magnetic resonance spectral study. Chem. Pharm. Bull. (1984), 32(2), 452–6.] and a number of 3-acetamido carbazoles with further amino- and nitro-substitution on the carbazole ring has been described [Lancelot, Jean Charles; Gazengel, Jean Marie; Robba, Max.; Study of 3-acetamido-9-ethylcarbazole nitration reactions. J. Heterocycl. Chem. (1981), 18(7), 1281–5]. Simionescu et al. report on the synthesis and polymerization of N-(9-ethyl-3-carbazolyl)maleimide [71356-15-5], N-(9-ethyl-3-carbazolyl)acrylamide [71348-60-2], N-(9-ethyl-3-carbazolyl)methacrylamide [71348-61-3], (9-ethyl-3-carbazolyl)methyl acrylate [71348-64-6], and (9ethyl-3-carbazolyl)methyl methacrylate [67549-44-4] [Simionescu, C. I.; Percec, V. New carbazole-containing monomers and polymers. J. Polym. Sci., Polym. Chem. Ed. (1979), 17(8), 2287–97]. Likewise, Ott et. al [Ott, Robert; Pinter, Erfried; Kajtna, Peter. Studies on quinones, V. 1,4-Carbazolquinones from p-benzoquinone and primary aliphatic amines. The alleged and the real 2-methylaminobenzoquinone. Monatsh. Chem. (1979), 110(1), 51–62. CODEN: MOCMB7; ISSN: 0026-9247.] describes the synthesis of N-methyl-N-[1,4,6-tris(acetyloxy)-9-methyl-9H-carbazol-3-yl]-acetamide and N-propyl-N-[1,4,6-tris(acetyloxy)-9-propyl-9H-carbazol-3-yl]-acetamide.

Neuropeptide Y (NPY) and related peptides (such as pancreatic polypeptide and peptide YY) are broadly distributed in central and peripheral neurons and have a broad array of biological activity mediated through the NPY receptors that exist in a variety of tissues. NPY (and related peptides) affect the central nervous and cardiovascular systems, vasculature, hormonal secretions, renal, gastrointestinal and pulmonary systems and lipid, glucose and energy metabolism. NPY potently stimulates hyperphagia and induces insulin resistance. Thus NPY antagonists are useful in the treatment of:

obesity, eating and metabolic disorders: as bulimia and anorexia, type 2 diabetes, hyperlipidemia and cellulite;

diseases pertaining to the heart, blood vessels or the renal system: vasospasm, heart failure, shock, cardiac hypertrophy, increased blood pressure, angina, myocardial infarction, sudden cardiac death, arrhythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal tract;

cerebral diseases and diseases related to the central nervous system: cerebral infarction, neurodegeneration, impaired cognition, Alzheimer's disease, epilepsy, seizures, stroke, and conditions related to stroke, cerebral vasospasm and hemorrhage, depression, anxiety, schizophrenia, dementia, addiction and substance abuse including nicotine, cocaine and alcohol, attention deficit disorder, sleep disorders, seasonal affective disorder;

conditions related to pain or nociception;

disorders related to disruption of circadian rhythms including jet lag;

diseases related to abnormal gastrointestinal motility and secretion: ileus, diarrhea, fecal incontinence, gastric ulcer, neurogenic voiding dysfunction, urinary incontinence, Crohn's disease, irritable bowel syndrome, inflammatory bowel disease, nausea and emesis;

conditions related to sexual dysfunction, reproductive disorders, and fertility;

conditions or disorders associated with inflammation;

respiratory diseases: asthma and conditions related to asthma and bronchoconstriction, nasal congestion, allergies, seasonal allergies; and diseases related to abnormal hormone release: luteinizing hormone, growth hormone, insulin, and prolactin.

In addition, those skilled in the art will appreciate that there will be benefits attendant to the weight loss including improvements in the comorbidities associated with obesity including insulin resistance, impaired glucose tolerance, Type II Diabetes, hypertension, hyperlipidemia, cardiovascular disease, gall stones, certain cancers, and sleep apnea.

SUMMARY OF THE INVENTION

This invention provides a compound of Formula I

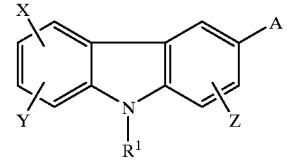

wherein X, Y, and Z are independently selected from
(a) hydrogen;
(b) halogen;
(c) hydroxy;
(d) nitro;
(e) cyano;
(f) $C_1$–$C_6$ alkyl;
(g) $C_1$–$C_6$ alkoxy;
(h) —$NR^7R^8$;
(i) —$CH_2NR^7R^8$;
(j) —$CH_2OR^7$;
(k) —$C(O)NR^7R^8$;
(l) $C_1$–$C_6$ alkylaryl; and
substituents X and Y, when ortho to each other, may be joined to form a ring, which may optionally include up to two heteroatoms selected from O, $NR^2$ or S;

$R^1$ is $C_1$–$C_5$ alkyl, alkylaryl, alkenyl, (cycloalkyl)alkyl, or mono or polyfluoroalkyl;

and A is $NR^2COR^3$, $CONR^2R^3$, or $NR^2SO_2R^3$ wherein:

$R^2$ is hydrogen, $C_1$–$C_3$ alkyl, $C_1$–$C_3$ alkylaryl, $C_1$–$C_3$ alkylheteroaryl, $C_2$–$C_4$ alkeny, $C_2$–$C_4$ alkynyl, or $C_1$–$C_5$ polyfluoroalkyl;

$R^3$ is selected from $C_1$–$C_6$ mono or polyfluoroalkyl, heteroaryl, $C_1$–$C_6$ alkyl (excluding $CH_3$), $C_3$–$C_8$ cycloalkyl, $C_2$–$C_6$ alkenyl, $C_5$–$C_8$ cycloalkenyl, $C_2$–$C_6$ alkynyl, or $C_4$–$C_8$ cycloazaalkyl; wherein $C_1$–$C_6$ alkyl, $C_3-C_8$ cycloalkyl, $C_2-C_6$ alkenyl, $C_5-C_8$ cycloalkenyl, $C_2-C_6$ alkynyl, or $C_4-C_8$ cycloazaalkyl can be independently substituted with one to three substituents selected from the group consisting of F, Br, Cl, aryl, heteroaryl, aryloxy, heteroaryloxy, $NR_4R_5$, $(C_1-C_6)$ alkoxy, $NO_2$, OH, CN, COOH, and $C_1-C_6$ thioalkyl.

$R^4$ and $R^5$ are selected independently from H, $C_1$–$C_6$ alkyl, $C_2-C_6$ alkenyl, $C_3-C_6$ cycloalkyl, $C_5-C_8$ cycloalkenyl, $C_2-C_6$ alkynyl, aryl, heteroaryl, alkylaryl, alkylheteroaryl; optionally substituted with 1–2 substituents independently selected from $R^6$; or $R^4$ and $R^5$ are taken together to be $C_3-C_8$ cycloalkyl, optionally substituted with 1–2 substituents independently selected from $R^6$; $C_5-C_8$ cycloalkenyl, optionally substituted with 1–2 substituents independently selected from $R^6$; or a heterocyclic ring containing up to two heteroatoms selected from the group consisting of —O—, —$NR^7$—, and —(O)m— (m=0–2), optionally substituted with 1–3 substituents independently selected from $R^6$;

$R^6$ is selected independently from hydrogen; halogen; nitro; cyano; hydroxy, $C_1-C_6$ alkyl; $C_1-C_6$ hydroxyalkyl, $C_1-C_6$ aminoalkyl, aryl, heteroaryl, aryloxy, heteroaryloxy, alkoxy; acyloxy; $C_1-C_4$ alkylthio; mono-, di-, or trihaloalkyl, or $(CH_2)_n NR^7R^8$ where n is 1–3.

$R^7$ and $R^8$ are independently selected from $C_1-C_6$ alkyl; $C_2-C_6$ alkenyl; $C_2-C_6$ alkynyl, aryl, or heteroaryl, and may be joined to form a carbocyclic or hetercyclic ring; which may optionally include up to two heteroatoms selected from O, $NR^2$, or S, and optical and geometric isomers thereof or tautomeric isomers thereof; and nontoxic pharmacologically acceptable acid addition salts, N-oxides, esters, and quaternary ammonium salts thereof; and with the proviso that if $R_1$ is $C_1-C_5$ alkyl and A is —$CONR_2R_3$, then when one of $R_2$ or $R_3$ is an azacycloalkyl alkyl group, the other of $R_2$ and $R_3$ must be a group other than hydrogen or $C_1-C_6$ alkyl.

In another aspect this invention provides a compound of the formula

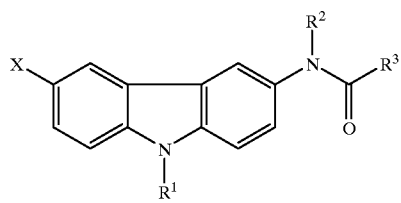

II where

X is selected from hydrogen; halogen; alkoxy; $NR^7R^8$; —$CH_2 NR^7R^8$; —$CH_2OR^7$; and —$C(O)NR^7R^8$;

$R^1$ is $C_1-C_5$ alkyl, alkenyl, alkylaryl or (cycloalkyl)alkyl, or mono or polyfluoroalkyl;

$R^2$ is hydrogen or $C_1-C_3$ alkyl;

$R^3$ is selected from $CF_3$; heteroaryl, $C_1-C_6$ alkyl (excluding $CH_3$), $C_3-C_8$ cycloalkyl, $C_2-C_6$ alkenyl, $C_5-C_8$ cycloalkenyl, $C_2-C_6$ alkynyl, or $C_4-C_8$ cycloazaalkyl; wherein $C_1-C_6$ alkyl, $C_3-C_8$ cycloalkyl, $C_2-C_6$ alkenyl, $C_5-C_8$ cycloalkenyl, $C_2-C_6$ alkynyl, or $C_4-C_8$ cycloazaalkyl can be independently substituted with one to three substituents selected from the group consisting of F, Br, Cl, aryl, heteroaryl, aryloxy, heteroaryloxy, $NR^4R^5$, $(C_1-C_6)$alkoxy, $NO_2$, OH, CN, COOH, and thioalkyl, where $R^4$ and $R^5$ are as defined above.

In another aspect this invention provides a compound of formula II wherein X is hydrogen or halogen; $R^1$ is methyl, ethyl, propyl, cyclopropylmethyl, or isopropyl; $R^2$ is hydrogen, and $R^3$ is selected from $C_1-C_3$ alkyl which can be independently substituted with one to two substituents selected from the group consisting of aryl, heteroaryl, $NR^4R^5$, $(C_1-C_6)$alkoxy, aryloxy, heteroaryloxy, or OH where $R^4$ and $R^5$ are as defined above, and optical and geometric isomers tautomeric isomers thereof; and nontoxic pharmacologically acceptable acid addition salts, N-oxides, esters, and quaternary ammonium salts thereof.

In another aspect this invention claims a compound of the formula

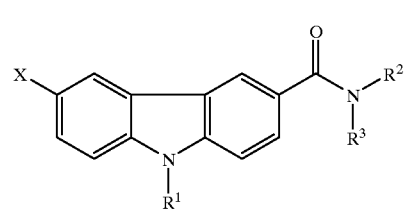

III where

X is selected from hydrogen; halogen; alkoxy; $NR^7R^8$; —$CH_2 NR^7R^8$; —$CH_2OR^7$; and —$C(O)NR^7R^8$;

$R^1$ is $C_1-C_6$ alkyl, $C_1-C_6$ alkenyl, $C_1-C_6$ alkylaryl or $C_1-C_6$ (cycloalkyl)alkyl, or mono or polyfluoroalkyl;

$R^2$ is hydrogen or $C_1-C_3$ alkyl, or mono or $C_1-C_6$ polyfluoroalkyl;

$R^3$ is selected from $C_1-C_5$ alkyl which can be independently substituted with one to two substituents selected from the group consisting of aryl, heteroaryl, $NR^4R^5$, $(C_1-C_6)$alkoxy, aryloxy, heteroaryloxy, or OH where $R^4$ and $R^5$ are as defined above, and optical and geometric tautomeric isomers thereof; and nontoxic pharmacologically acceptable acid addition salts, N-oxides, esters, and quaternary ammonium salts thereof.

This invention also provides a compound of formula III wherein X is hydrogen or halogen; $R^1$ is methyl, ethyl, or isopropyl; $R^2$ is hydrogen, and $R^3$ is selected from $C_1-C_5$ alkyl which can be independently substituted with one to two substituents selected from the group consisting of aryl, heteroaryl, $NR^4R^5$, $(C_1-C_6)$alkoxy, aryloxy, heteroaryloxy, or OH where $R^4$ and $R^5$ are as defined above, and optical and geometric isomers and tautomeric thereof; and nontoxic pharmacologically acceptable acid addition salts, N-oxides, esters, and quaternary ammonium salts thereof.

This invention also provides a compound of the formula

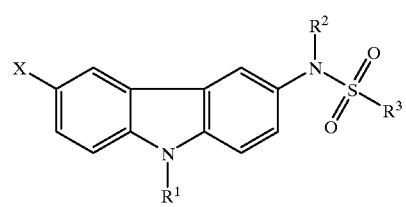

IV where

X is selected from hydrogen; halogen; alkoxy; $NR^7R^8$; —$CH_2 NR^7R^8$; —$CH_2OR^7$; and —$C(O)NR^7R^8$;

$R^1$ is $C_1-C_6$ alkyl, alkenyl, alkylaryl, (cycloalkyl)alkyl mono or polyfluoroalkyl;

$R^2$ is hydrogen or $C_1$–$C_3$ alkyl;

$R^3$ is selected from $C_1$–$C_6$ mono or polyfluoroalkyl, heteroaryl, $C_1$–$C_6$ alkyl (excluding $CH_3$), $C_3$–$C_8$ cycloalkyl, $C_2$–$C_6$ alkenyl, $C_5$–$C_8$ cycloalkenyl, $C_2$–$C_6$ alkynyl, or $C_4$–$C_8$ cycloazaalkyl; wherein $C_1$–$C_6$ alkyl, $C_3$–$C_8$ cycloalkyl, $C_2$–$C_6$ alkenyl, $C_5$–$C_8$ cycloalkenyl, $C_2$–$C_6$ alkynyl, or $C_4$–$C_8$ cycloazaalkyl can be independently substituted with one to three substituents selected from the group consisting of F, Br, Cl, aryl, heteroaryl, aryloxy, heteroaryloxy, $NR^4R^5$, ($C_1$–$C_6$) alkoxy, $NO_2$, OH, CN, COOH, and $C_1$–$C_6$ thioalkyl; where $R^4$ and $R^5$ are as defined above, and optical and geometric isomers and tautomeric thereof; and non-toxic pharmacologically acceptable acid addition salts, N-oxides, esters, and quaternary ammonium salts thereof.

This invention also provides a compound of formula IV wherein X is hydrogen or halogen; $R^1$ is methyl, ethyl, or isopropyl; $R^2$ is hydrogen, and $R^3$ is selected from $C_1$–$C_6$ alkyl which can be independently substituted with one to two substituents selected from the group consisting of aryl, heteroaryl, aryloxy, heteroaryloxy, $NR^4R^5$, ($C_1$–$C_6$)alkoxy, or OH where $R^4$ and $R^5$ are as defined above, and optical and geometric isomers or tautomeric isomers thereof; and non-toxic pharmacologically acceptable acid addition salts, N-oxides, esters, and quaternary ammonium salts thereof.

This invention also provides a pharmaceutical composition for treating or preventing obesity comprising a compound of formulae I, II, III or IV and a pharmaceutically acceptable carrier.

In another aspect, this invention relates to a method of inhibiting or alleviating a pathological condition or physiological disorder in a mammal characterized by or associated with an excess of neuropeptide Y which comprises administering to a mammal in need of such treatment a neuropeptide Y inhibitor of the compound of Formulae I, II, III or IV shown above.

This invention also relates to a method of treating a pathological condition wherein said pathological condition or physiological disorder is a feeding disorder including obesity and bulimia comprising administering to a mammal in need of such treatment a neuropeptide Y inhibitor of the compound of Formulae I, II, III or IV shown above.

In another aspect, this invention comprises a method of inhibiting or alleviating a pathological condition or physiological disorder in a mammal wherein said pathological condition or physiological disorder is selected from the group consisting of:

disorders or diseases pertaining to the heart, blood vessels or the renal system, such as vasospasm, heart failure, shock, cardiac hypertrophy, increased blood pressure, angina, myocardial infarction, sudden cardiac death, arrhythmia, peripheral vascular disease, and abnormal renal conditions such as impaired flow of fluid, abnormal mass transport, and renal failure;

conditions related to increased sympathetic nerve activity for example, during or after coronary artery surgery, and operations and surgery in the gastrointestinal tract;

cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia;

conditions related to pain or nociception;

diseases related to abnormal gastrointestinal motility and secretion, such as different forms of ileus, urinary incontinence, and Crohn's disease;

lipid related disorders including hypocholesterolemia, hyperlipidemia and arteriosclerosis;

abnormal drink and food intake disorders, such as anorexia and metabolic disorders; diseases related to sexual dysfunction and reproductive disorders;

conditions or disorders associated with inflammation;

respiratory diseases, such as asthma and conditions related to asthma and bronchoconstriction; and diseases related to abnormal hormone release, such as leutinizing hormone, growth hormone, insulin, and prolactin comprising administering to a mammal in need of such treatment a neuropeptide Y inhibiting amount of the compound of Formulae I, II, III or IV shown above.

Compounds of formula I containing a basic nitrogen are capable of forming a wide variety of salts with various inorganic and organic acids. The acids that may be used to prepare pharmaceutically acceptable acid addition salts of the compound of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, fumarate, gluconate, glucaronate, saccharate, formate, benzoate, glutamate, methanesulfonate, ethanesulfonate, benzenesulfonate, and p-toluenesulfonate.

This invention also provides a compound selected from the group consisting of:

2-Dimethylamino-N-(9-ethyl-9H-carbazol-3-yl)-acetamide;

3-Diethylamino-N-(9-ethyl-9H-carbazol-3-yl)-propionamide;

N-(9-Ethyl-9H-carbazol-3-yl)-2-fluoro-benzamide;

2-Pyridin-2-yl-thiazole-4-carboxylic acid (9-ethyl-9H-carbazol-3-yl)-amide;

N-(9-Ethyl-9H-carbazol-3-yl)-2-pyridin-2-yl-acetamide;

N-(9-Ethyl-9H-carbazol-3-yl)-2-pyridin-3-yl-acetamide;

N-(9-Ethyl-9H-carbazol-3-yl)-isonicotinamide;

1H-Indole-2-carboxylic acid (9-ethyl-9H-carbazol-3-yl)-amide;

4-Dimethylamino-N-(9-ethyl-9H-carbazol-3-yl)-butyramide;

N-(9-Ethyl-9H-carbazol-3-yl)-2-pyridin-4-yl-acetamide;

N-(9-Ethyl-9H-carbazol-3-yl)-2-piperidin-1-yl-acetamide;

N-(9-Ethyl-9H-carbazol-3-yl)-3-morpholin-4-yl-propionamide;

N-(9-Ethyl-9H-carbazol-3-yl)-3-piperidin-1-yl-propionamide;

N-(9-Ethyl-9H-carbazol-3-yl)-2-hydroxy-2,2-diphenyl-acetamide;

N-(9-Ethyl-9H-carbazol-3-yl)-2-hydroxy-2-methyl-propionamide;

N-(9-Ethyl-9H-carbazol-3-yl)-2-hydroxy-2-methyl-butyramide;

N-(9-Ethyl-9H-carbazol-3-yl)-2-hydroxy-2-phenyl-propionamide;

(R)-N-(9-Ethyl-9H-carbazol-3-yl)-2-hydroxy-2-phenyl-propionamide;

2-Bromo-N-(9-ethyl-9H-carbazol-3-yl)-acetamide; and

3-Dimethylamino-N-(9-ethyl-9H-carbazol-3-yl)-propionamide.

This invention also provides a compound selected from the group consisting of:

N-(9-Ethyl-9H-carbazol-3-yl)-2-[1,2,4]triazol-1-yl-acetamide;

N-(9-Ethyl-9H-carbazol-3-yl)-2-(4-methyl-piperazin-1-yl)-acetamide;

2-[Bis-(2-hydroxy-ethyl)-amino]-N-(9-ethyl-9H-carbazol-3-yl)-acetamide;
N-(9-Ethyl-9H-carbazol-3-yl)-2-pyrrolidin-1-yl-acetamide;
2-Benzylamino-N-(9-ethyl-9H-carbazol-3-yl)-acetamide;
N-(9-Ethyl-9H-carbazol-3-yl)-3-(4-phenyl-piperidin-1-yl)-propionamide;
3-(3,4-Dihydro-1H-isoquinolin-2-yl)-N-(9-ethyl-9H-carbazol-3-yl) propionamide;
3-(2,5-Dihydro-pyrrol-1-yl)-N-(9-ethyl-9H-carbazol-3-yl)-propionamide;
N-(9-Ethyl-9H-carbazol-3-yl)-3-indol-1-yl-propionamide;
3-Diphenylamino-N-(9-ethyl-9H-carbazol-3-yl)-propionamide;
3-(5-Chloro-quinolin-8-yloxy)-N-(9-ethyl-9H-carbazol-3-yl)-propionamide;
3-Carbazol-9-yl-N-(9-ethyl-9H-carbazol-3-yl)-propionamide;
N-(9-Ethyl-9H-carbazol-3-yl)-3-(4-piperidin-1-ylmethyl-phenoxy)-propionamide;
N-(9-Ethyl-9H-carbazol-3-yl)-3-[methyl-(1,2,3,4-tetrahydro-naphthalen-2-yl)-amino]-propionamide;
N-(9-Ethyl-9H-carbazol-3-yl)-3-(quinolin-7-yloxy)-propionamide;
N-(9-Ethyl-9H-carbazol-3-yl)-3-pyrrolidin-1-yl-propionamide;
2-[Bis-(2-hydroxy-ethyl)-amino]-N-(9-ethyl-9H-carbazol-3-yl)-acetamide;
2-[4-(4-Chloro-phenyl)-4-hydroxy-piperidin-1-yl]-N-(9-ethyl-9H-carbazol-3-yl)-acetamide; and
N-(9-Ethyl-9H-carbazol-3-yl)-2-(4-hydroxy-4-phenyl-piperidin-1-yl)-acetamide.

This invention also provides a compound selected from the group consisting of:
3-Bromo-N-(9-ethyl-9H-carbazol-3-yl)-propionamide;
N-(9-Isopropyl-9H-carbazol-3-yl)-trifluoroacetamide;
N-(9-Isopropyl-9H-carbazol-3-yl)-3-(4-phenyl-piperidin-1-yl)-propionamide;
N-(9-Ethyl-9H-carbazol-3-yl)-3-(4-hydroxy-4-phenyl-piperidin-1-yl)-propionamide;
3-[4-(4-Chloro-phenyl)-4-hydroxy-piperidin-1-yl]-N-(9-ethyl-9H-carbazol-3-yl)-propionamide;
4-Dimethylamino-N-(9-ethyl-9H-carbazol-3-yl)-N-methyl-butyramide;
3-[1,4']Bipiperidinyl-1'-yl-N-(9-ethyl-9H-carbazol-3-yl)-propionamide;
N-(9-Ethyl-9H-carbazol-3-yl)-3-(4-phenyl-piperazin-1-yl)-propionamide;
3-(4-Benzyl-piperidin-1-yl)-N-(9-ethyl-9H-carbazol-3-yl)-propionamide;
3-(4-Dimethylamino-piperidin-1-yl)-N-(9-ethyl-9H-carbazol-3-yl)-propionamide;
3-(4-Dimethylaminoethyl-piperidin-1-yl)-N-(9-ethyl-9H-carbazol-3-yl)-propionamide;
N-(9-Methyl-9H-carbazol-3-yl)-trifluoroacetamide;
1-Hydroxy-cyclopropanecarboxylic acid (9-ethyl-9H-carbazol-3-yl)-amide;
N-(9-Ethyl-9H-carbazol-3-yl)-3-(4-cyano-4-phenyl-piperidin-1-yl)-propionamide;
2-(4-Chloro)-benzylamino-N-(9-ethyl-9H-carbazol-3-yl)-acetamide;
N-(9-Ethyl-9H-carbazol-3-yl)-2-(4-phenyl-piperidin-1-yl)-acetamide;
N-(9-Ethyl-9H-carbazol-3-yl)-2-(4-(4-fluoro)-phenyl-piperazin-1-yl)-acetamide;
N-(9-Ethyl-9H-carbazol-3-yl)-2-(4-pyridin-2-yl-piperazin-1-yl)-acetamide;
N-(9-Ethyl-9H-carbazol-3-yl)-3-(4-pyridin-2-yl-piperazin-1-yl)-propionamide; and
N-(9-Ethyl-9H-carbazol-3-yl)-3-(4-(4-fluoro)-phenyl-piperazin-1-yl)-propionamide.

This invention also provides a compound selected from the group consisting of:
2-(4-fluoro)-benzylamino-N-(9-ethyl-9H-carbazol-3-yl)-acetamide;
(R)-N-(9-Ethyl-9H-carbazol-3-yl)-2-(1-phenyl-ethylamino)-acetamide;
(R)-N-(9-Ethyl-9H-carbazol-3-yl)-2-(1-(4-chloro)-phenyl-ethylamino)-acetamide;
N-(9-isopropyl-9H-carbazol-3-yl)-3-pyrrolidin-1-yl-propionamide;
2-(3-Diethylamino-2-hydroxy-propylamino)-N-(9-ethyl-9H-carbazol-3-yl)-acetamide;
2-(Benzyl-isopropyl-amino)-N-(9-ethyl-9H-carbazol-3-yl)-acetamide;
N-(9-Ethyl-9H-carbazol-3-yl)-2-(4-pyrrolidin-1-yl-piperidin-1-yl)-acetamide;
N-(9-Ethyl-9H-carbazol-3-yl)-2-(6-isopropylamino-3-aza-bicyclo[3.1.0]hex-3-yl)-acetamide;
N-(9-Ethyl-9H-carbazol-3-yl)-2-(6-amino-3-aza-bicyclo[3.1.0]hex-3-yl)-acetamide;
N-(9-Ethyl-9H-carbazol-3-yl)-2-(6-benzylamino-3-aza-bicyclo[3.1.0]hex-3-yl)-acetamide;
N-(9-Ethyl-9H-carbazol-3-yl)-2-(6-isobutylamino-3-aza-bicyclo[3.1.0]hex-3-yl)-acetamide;
N-3-Bromo-(9-ethyl-9H-carbazol-6-yl)-trifluoroacetamide;
N-(9-Ethyl-6formyl-9H-carbazol-3-yl)-trifluoroacetamide;
N-(9-Ethyl-6-hydroxymethyl-9H-carbazol-3-yl)-trifluoroacetamide;
N-(9-Ethyl-9H-carbazol-3-yl)-methanesulfonamide;
N-[6-(3,4-Dihydro-1H-isoquinolin-2-ylmethyl)-9-ethyl-9H-carbazol-3-yl]-trifluoro-acetamide;
N-(9-Ethyl-9H-carbazol-3-yl)-chloromethanesulfonamide;
N-(9-Ethyl-9H-carbazol-3-yl)-2-pyridin-3-yl-N-methylacetamide;
2-Bromo-N-(9-ethyl-9H-carbazol-3-yl)-acetamide; and
3-Dimethylamino-N-(9-ethyl-9H-carbazol-3-yl)-propionamide.

This invention also provides a compound selected from the group consisting of:
N-(9-Ethyl-9H-carbazol-3-yl)-2-[1,2,4]triazol-1-yl-acetamide;
N-(9-Ethyl-9H-carbazol-3-yl)-2-(4-methyl-piperazin-1-yl)-acetamide;
2-[Bis-(2-hydroxy-ethyl)-amino]-N-(9-ethyl-9H-carbazol-3-yl)-acetamide;
N-(9-Ethyl-9H-carbazol-3-yl)-2-pyrrolidin-1-yl-acetamide;
2-Benzylamino-N-(9-ethyl-9H-carbazol-3-yl)-acetamide;
N-(9-Ethyl-9H-carbazol-3-yl)-3-(4-phenyl-piperidin-1-yl)-propionamide;
3-(3,4-Dihydro-1H-isoquinolin-2-yl)-N-(9-ethyl-9H-carbazol-3-yl)-propionamide;
3-(2,5-Dihydro-pyrrol-1-yl)-N-(9-ethyl-9H-carbazol-3-yl)-propionamide;
N-(9-Ethyl-9H-carbazol-3-yl)-3-indol-1-yl-propionamide;
3-Diphenylamino-N-(9-ethyl-9H-carbazol-3-yl)-propionamide;
3-(5-Chloro-quinolin-8-yloxy)-N-(9-ethyl-9H-carbazol-3-yl)-propionamide;
3-Carbazol-9-yl-N-(9-ethyl-9H-carbazol-3-yl)-propionamide;
N-(9-Ethyl-9H-carbazol-3-yl)-3-(4-piperidin-1-ylmethyl-phenoxy)-propionamide;
N-(9-Ethyl-9H-carbazol-3-yl)-3-[methyl-(1,2,3,4-tetrahydro-naphthalen-2-yl)-amino]-propionamide;
N-(9-Ethyl-9H-carbazol-3-yl)-3-(quinolin-7-yloxy)-propionamide;

N-(9-Ethyl-9H-carbazol-3-yl)-3-pyrrolidin-1-yl-propionamide;
2-[Bis-(2-hydroxy-ethyl)-amino]-N-(9-ethyl-9H-carbazol-3-yl)-acetamide;
2-[4-(4-Chloro-phenyl)-4-hydroxy-piperidin-1-yl]-N-(9-ethyl-9H-carbazol-3-yl)-acetamide;
N-(9-Ethyl-9H-carbazol-3-yl)-2-(4-hydroxyl-4-phenyl-piperidin-1-yl)-acetamide;
3-Bromo-N-(9-ethyl-9H-carbazol-3-yl)-propionamide; and
4- N-(9-Isopropyl-9H-carbazol-3-yl)-acetamide.

This invention also provides a compound selected from the group consisting of:
N-(9-Isopropyl-9H-carbazol-3-yl)-3-(4-phenyl-piperidin-1-yl)-propionamide;
N-(9-Ethyl-9H-carbazol-3-yl)-3-(4-hydroxy-4-phenyl-piperidin-1-yl)-propionamide;
3-[4-(4-Chloro-phenyl)-4-hydroxy-piperidin-1-yl]-N-(9-ethyl-9H-carbazol-3-yl)-propionamide;
4-Dimethylamino-N-(9-ethyl-9H-carbazol-3-yl)-N-methyl-butyramide;
3-[1,4']Bipiperidinyl-1'-yl-N-(9-ethyl-9H-carbazol-3-yl)-propionamide;
N-(9-Ethyl-9H-carbazol-3-yl)-3-(4-phenyl-piperazin-1-yl)-propionamide;
3-(4-Benzyl-piperidin-1-yl)-N-(9-ethyl-9H-carbazol-3-yl)-propionamide;
3-(4-Dimethylamino-piperidin-1-yl)-N-(9-ethyl-9H-carbazol-3-yl)-propionamide;
3-(4-Dimethylaminoethyl-piperidin-1-yl)-N-(9-ethyl-9H-carbazol-3-yl)-propionamide;
N-(9-Methyl-9H-carbazol-3-yl)-trifluoroacetamide;
1-Hydroxy-cyclopropanecarboxylic acid (9-ethyl-9H-carbazol-3-yl)-amide;
N-(9-Ethyl-9H-carbazol-3-yl)-3-(4-cyano-4-phenyl-piperidin-1-yl)-propionamide;
2-(4-Chloro)-benzylamino-N-(9-ethyl-9H-carbazol-3-yl)-acetamide;
N-(9-Ethyl-9H-carbazol-3-yl)-2-(4-phenyl-piperidin-1-yl)-acetamide;
N-(9-Ethyl-9H-carbazol-3-yl)-2-(4-(4-fluoro)-phenyl-piperazin-1-yl)-acetamide;
N-(9-Ethyl-9H-carbazol-3-yl)-2-(4-pyridin-2-yl-piperazin-1-yl)-acetamide;
N-(9-Ethyl-9H-carbazol-3-yl)-2-(4-pyridin-2-yl-piperazin-1-yl)-propionamide;
N-(9-Ethyl-9H-carbazol-3-yl)-3-(4-(4-fluoro)-phenyl-piperazin-1-yl)-propionamide; and
2-(4-fluoro)-benzylamino-N-(9-ethyl-9H-carbazol-3-yl)-acetamide.

This invention also provides a compound selected from the group consisting of:
(R)-N-(9-Ethyl-9H-carbazol-3-yl)-2-(1-phenyl-ethylamino)-acetamide;
(R)-N-(9-Ethyl-9H-carbazol-3-yl)-2-(1-(4-chloro)-phenyl-ethylamino)-acetamide;
N-(9-isopropyl-9H-carbazol-3-yl)-3-pyrrolidin-1-yl-propionamide;
(R)- or (S)-N-(9-Ethyl-9H-carbazol-3-yl)-2-(oxiranylmethyl-amino)-acetamide;
(S), (R), or a mixture of (S) and (R) 2-(3-Diethylamino-2-hydroxy-propylamino)-N-(9-ethyl-9H-carbazol-3-yl)-acetamide;
(S)-N-(6-tert-Butyl-9-ethyl-9H-carbazol-3-yl)-2-(3-diethylamino-2-hydroxy-propylamino)-acetamide
2-(Benzyl-isopropyl-amino)-N-(9-ethyl-9H-carbazol-3-yl)-acetamide;
N-(9-Ethyl-9H-carbazol-3-yl)-2-(4-pyrrolidin-1-yl-piperidin-1-yl)-acetamide;
N-(9-Ethyl-9H-carbazol-3-yl)-2-(6-isopropylamino-3-aza-bicyclo[3.1.0]hex-3-yl)-acetamide;
N-(9-Ethyl-9H-carbazol-3-yl)-2-(6-amino-3-aza-bicyclo[3.1.0]hex-3-yl)-acetamide;
N-(9-Ethyl-9H-carbazol-3-yl)-2-(6-benzylamino-3-aza-bicyclo[3.1.0]hex-3-yl)-acetamide;
N-(9-Ethyl-9H-carbazol-3-yl)-2-(6-isobutylamino-3-aza-bicyclo[3.1.0]hex-3-yl)-acetamide;
N-3-Bromo-(9-ethyl-9H-carbazol-6-yl)-trifluoroacetamide;
N-(9-Ethyl-6-formyl-9H-carbazol-3-yl)-trifluoroacetamide;
N-(9-Ethyl-6-hydroxymethyl-9H-carbazol-3-yl)-trifluoroacetamide;
N-[6-(3,4-Dihydro-1H-isoquinolin-2-ylmethyl)-9-ethyl-9H-carbazol-3-yl]-trifluoroacetamide;
N-(9-Ethyl-9H-carbazol-3-yl)-2-pyridin-3-yl-N-methylacetamide;
9-Ethyl-9H-carbazole-3-carboxylic acid (pyridin-3-ylmethyl)-amide;
(9-Ethyl-9H-carbazol-3-yl)-(4-hydroxyl-4-phenyl-piperidin-1-yl)-methanone;
9-Ethyl-9H-carbazole-3-carboxylic acid (2-benzylamino-ethyl)-amide;
9-Ethyl-9H-carbazole-3-carboxylic acid benzylamide; and
9-Ethyl-9H-carbazole-3-carboxylic acid (3-morpholin-4-yl-propyl)-amide.

This invention also provides a compound selected from the group consisting of:
9-Ethyl-9H-carbazole-3-carboxylic acid (1-benzyl-pyrrolidin-3-yl)-amide;
9-Ethyl-9H-carbazole-3-carboxylic acid (2-isopropylamino-ethyl)-amide;
9-Ethyl-9H-carbazole-3-carboxylic acid (2-hydroxy-ethyl)-amide;
N-(9-Ethyl-9H-carbazol-3-yl)-methanesulfonamide;
N-(9-Ethyl-9H-carbazol-3-yl)-chloromethanesulfonamide;
9-Ethyl-9H-carbazole-3-carboxylic acid [2-(bis-pyridin-4-ylmethyl-amino)-ethyl]-amide;
9-Ethyl-9H-carbazole-3-carboxylic acid {2-[bis-(1-methyl-1H-indol-3-ylmethyl)-amino]-ethyl}-amide;
9-Ethyl-9H-carbazole-3-carboxylic acid {2-[(thiazol-2-ylmethyl)-amino]-ethyl}-amide;
9-Ethyl-9H-carbazole-3-carboxylic acid [2-(bis-quinolin-2-ylmethyl-amino)-ethyl]-amide;
9-Ethyl-9H-carbazole-3-carboxylic acid {2-[(quinolin-2-ylmethyl)-amino]-ethyl}-amide;
9-Ethyl-9H-carbazole-3-carboxylic acid phenethyl-amide;
9-Ethyl-9H-carbazole-3-carboxylic acid (3-phenyl-propyl)-amide;
9-Ethyl-9H-carbazole-3-carboxylic acid (2-diisopropylamino-ethyl)-amide; and
9-Ethyl-9H-carbazole-3-carboxylic acid [3-(2-methyl-piperidin-1-yl)-propyl]-amide.

The present invention also encompasses the prodrugs of the compounds of Formula I–IV. Those skilled in the art will recognize various synthetic methodologies which may be employed to prepare non-toxic pharmaceutically acceptable addition salts and prodrugs of the compounds encompassed by Formula I–IV.

DETAILED DESCRIPTION OF THE INVENTION

By "aryl" and "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can optionally be unsubstituted or substituted with 1–2 substituents related from e.g., halogen, lower alkyl, lower alkoxy, lower alkylthio, trifluoromethyl, lower acyloxy, aryl, heteroaryl, and hydroxy.

By "alkyl" and "lower alkyl" is meant straight and branched chain alkyl groups having from 1–6 carbon atoms.

By "lower alkoxy" and "alkoxy" is meant straight and branched chain alkoxy groups having from 1–6 carbon atoms.

By "halogen" is meant fluorine, chlorine, bromine and iodine.

By "heteroaryl" is meant a heterocycle in which at least one heterocyclic ring is aromatic By "Alkylaryl" is meant an alkyl group where (R) is a lower alkyl group containing at least an aryl group By "alkyl heteroaryl" is meant an alkyl group where (R) is a lower alkyl group containing (bound to) at least one heteroaryl group By "aryloxy" is meant a compound where oxygen is bound to an aryl group By "heteroaryloxy" is meant a compound where oxygen is bound to a heteroaryl group By "heterocycle" is meant a saturated, unsaturated, or aromatic carbocyclic group having one or more rings and having at least one heteroatom, such as N, S, or O, within the ring; optionally substituted with other functionalities.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The expression "pharmaceutically acceptable acid addition salts" is intended to include but is not limited to such salts as the hydrochloride, hydrobromide, hydroiodide, nitrate, hydrogen sulfate, dihydrogen phosphate, mesylate, maleate, and succinate. Such salts are conventionally prepared by reacting the free base form of the compound (I), (II) or (III) with an appropriate acid, usually one molar equivalent, and in a solvent. Those salts which do not precipitate directly are generally isolated by concentration of the solvent and/or addition of a non-solvent.

The expression "prodrug" refers to compounds that are drug precursors, which, following administration, release the drug in vivo via a chemical or physiological process (e.g., a prodrug on being brought to the physiological pH is converted to the desired drug form).

As used herein, the expressions "reaction-inert solvent" and "inert solvent" refers to a solvent or mixture of solvents which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates and solvates are also included.

Diasteromeric mixtures can be separated into their individual diastereomers on the basis of their physical chemical differences by methods known per se., for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

Other features and advantages will be apparent from the specification and claims which describe the invention.

An illustration of the preparation of compounds of the present invention is given in Schemes 1, 2 and 3. Those having skill in the art will recognize that the starting materials may be varied and additional steps employed to produce compounds encompassed by the present invention.

Preparation of Carbazoles

Scheme 1
Synthesis of 3-Acylamino Carbazoles

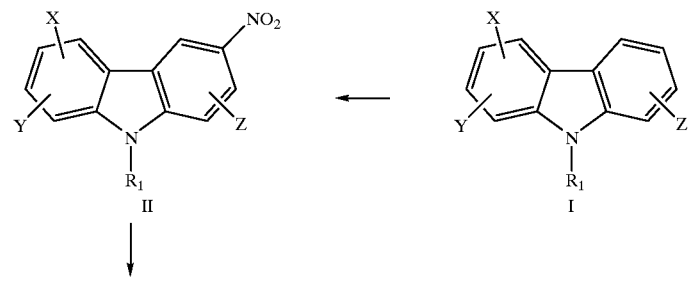

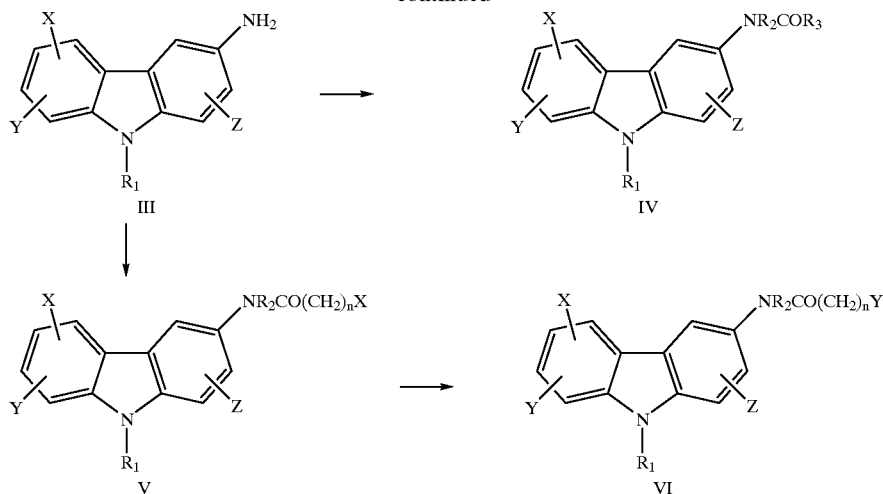

Reaction of an N-alkyl carbazole of the type I (Scheme 1; X;Y;Z=H) under standard nitration conditions (e.g. nitric acid/acid) affords the 3-nitro-N-alkyl carbazole II, with can be subsequently reduced under standard conditions (e.g. catalytic hydrogenation, SnCl$_2$, Zn/AcOH) to afford the desired 3-amino-N-alkyl carbazole III. Treatment of III with an activated acid derivative (e.g. acid chloride, acylimidazolide, N-hydroxybenzotriazole ester) or with a carboxylic acid in the presence of a coupling reagent (e.g. DCC, EDC) affords the acylated carbazole IV directly. Likewise, coupling of III with a haloalkyl carboxylic acid (e.g. X=Cl, Br, I) affords the haloamide V, which can be subsequently reacted with nucleophile (e.g. NHR$_5$R$_6$, ROH, ArOH, Het—OH) to afford carbazoles of the type VI (e.g. Y=NR$_5$R$_6$, OR, OAr, OHet). Alternatively, treatment of the aminocarbazole III when X; Y; and Z are hydrogen with and electrophile such as bromine selectively affords the 3-amino-6-bromo carbazole. The bromocarbazole can be further converted into a wide variety of C-6 modified 3-aminocarbazoles using standard organic reactions.

Scheme 2
Synthesis of 3-Aminocarbonyl Carbazoles

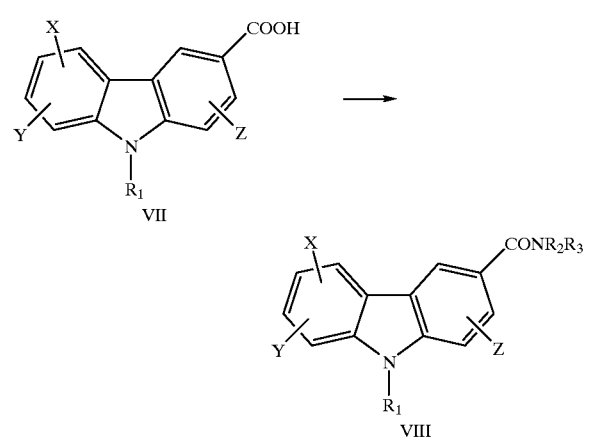

Activation of the carboxy group of the 3-carboxy carbazole VII (Scheme 2) using standard coupling reagents followed by treatment with a primary or secondary amine affords the desired 3-aminocarbonyl carbazole VIII. Thus, for example, treatment of the carboxylic acid in an organic solvent such as methylene chloride or DMF with a coupling reagent such as EDC or CDI followed by treatment with an amine HNR$_2$R$_3$ affords the desired amide VI.

Scheme 3
Synthesis of 3-Aminosulfonyl Carbazoles

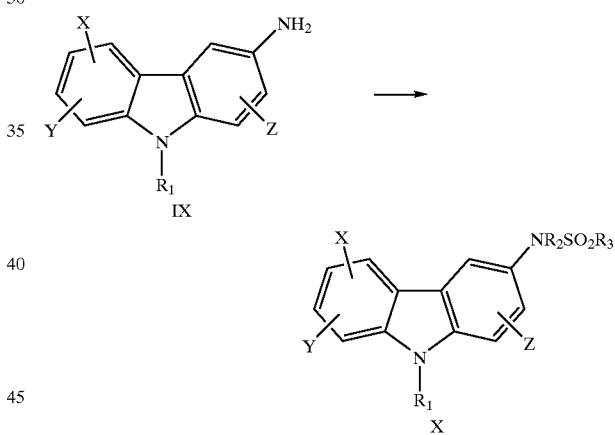

Sulfonylation of the 3-amino-N-alkyl carbazole under standard conditions (e.g. a sulfonyl chloride/base) affords the desired sulfonamide carbazole X.

Assay for NPY-5 Binding
[$^{125}$I]PYY Binding at Human NPY Receptors Expressed in Sf9 Cells Baculovirus-infected Sf9 cells expressing recombinant human NPY 5 receptors are harvested at 48 hours. At the time of harvest, cell pellets are resuspended in lysis buffer (20 mM Tris-HCl, pH 7.4, 5 mM EDTA, 0.5 μg/ml leupeptin, 2 μg/ml Aprotonin and 200 mM PMSF) and homogenized using a Polytron (setting 3, 25–30 seconds). Homogenates are centrifuged at 4° C. for 5 minutes at 200×g (~1.5 rpm) to pellet the nuclei. The supernatant is collected into a fresh tube and centrifuged at 48,000×g for 10 minutes. Pellets are washed once in lysis buffer and centrifuged. The final pellet is resuspended in PBS and stored in aliquots at −80° C. Purified membranes are washed using PBS and resuspended in binding buffer (50 mM Tris(HCl), pH 7.4, 5 mM KCl, 120 mM NaCl, 2 mM CaCl$_2$, 1 mM MgCl$_2$, 0.1% bovine serum albumin (BSA)). Membranes (20 μg/reaction tube) are added to polypropylene tubes containing 0.035 nM [$^{125}$I]PYY(porcine), displacers ranging from 10$^{-12}$ M to 10$^{-5}$ M, and buffer to yield a final volume of 0.5 mL. Nonspecific binding is determined in the presence of 1 μM NPY(human) and accounts for 10% of total binding. Following a 2 hour incubation at room temperature, the reaction is terminated by rapid vacuum filtration. Samples are filtered over presoaked GF/C Whatman filters (1.0% polyethylenemine) and rinsed 2 times with 5 mL cold binding buffer without BSA. A gamma counter is used to count filters with an efficiency of 85%. IC$_{50}$ values were calculated with the non-linear curve fitting program RS/1 (SigmaPlot, Jandel).

The compounds of this invention were found to have Ki values of less than 1 μM in the NPY-5 binding assay.

NPY5-CT [$^{125}$I]-PYY Protocol

I. Membrane Preparation for 500 mL Cell Suspension:

1) The sequence for the chimeric receptor was inserted into pBacPAK 9 vector (commercially available from Clontech) and then expressed in Baculovirus infected Sf9 cell line. Baculovirus-infected Sf9 cells expressing recombinant human NPY5 CT receptors are harvested at 48 hours. [NPY5 CT receptors are chimericY5/Y1 receptors containing amino acids 1–442 of the human Y5 receptor (the human Y5-receptor as described in U.S. Pat. No. 5,919,901) and the C-terminal amino acids 328–384 of the human Y1 receptor (Cloning and functional expression of a human neuropeptide Y/peptide YY receptor of the Y1 type. J Biol Chem. 1992 Jun 5;267(16):10935–8). The binding profile of these receptors is equivalent to native NPY5 receptors.)

2) At the time of harvest, resuspend each pellet in 30 mL of lysis buffer (20 mM Tris-HCl, pH 7.4, 5 mM EDTA, 0.5 μg/ml leupeptin, 2 μg/ml Aprotonin and 200 μM PMSF) and homogenize using a Polytron (setting 3, 25–30 seconds).

3) Centrifuge the homogenate at 4° C. for 5 minutes at 200×g (~1500 rpm) to pellet the nuclei. Collect the supernatant (and gently rinse the top of the pellet) into a fresh tube and centrifuge at 48,000×g for 10 minutes (20000 rpm).

4) The final pellet is resuspended in 10 mL of PBS and stored in aliquots at −80° C.

II. Solutions

| Rinse Buffer: | MW (g/mol) | 1L (g) | 10L (g) |
|---|---|---|---|
| 50 mM Tris 7.0 | 151.6 | 7.58 | 75.8 |
| 5 mM KCl | 74.55 | 0.372 | 3.72 |
| 120 mM NaCl | 58.44 | 7.0 | 70.0 |
| 2 mM CaCl$_2$ | 147.0 | 0.294 | 2.94 |

Assay Buffer
   Rinse buffer containing 0.1% BSA (1 g/L)

III. Assay Protocol

Components:
   150 ul Tissue Solution
   50 ul Ligand/GTP Solution
   20 ul humanNPY (Non-specific)
   2 ul Drug Incubate assay at room temperature for 2 hours. Terminate reaction using vacuum filtration over 1% PEI pretreated filters. Count filters in scintillation fluid. Specific binding ranges between 75% to 85%.

Tissue Preparation:
   Baculovirus-infected Sf9 cells expressing recombinant human NPY5 CT receptors are stored in stock aliquots. The protein concentrations vary from batch to batch.

Concentration:
   10–25 ug tissue/150 ul assay buffer (dependant upon signal received from saturation analysis of new material). The average used is 15 ug/well Ligand:
   Each 50 uCi of [$^{125}$I]PYY is reconstituted in 1 ml of 0.5% BSA in H$_2$O. The reconstituted PYY is then diluted in assay buffer such that a 5 ul count yields approx. 2800 cpm. Final Concentration: 30–35 pM /well GTP:
   GTP is stored in −20° C. freezer. A stock of 400 uM GTP is prepared in the [$^{125}$I]PYY ligand solution. The ligand/GTP solution is then added to the assay plates: 50 ul/well. Final Concentration: 100 uM/well Nonspecific:
   Human NPY is stored in the −20° C. freezer at 10-4M in a 0.1% BSA solution.
   Final concentration: 1 uM/well Additional Info.:
   Assay Format: Microtiter
   Pretreat filters in 1% PEI.

Description Of Artificial Sequence:Y5/Y1 CHIMERA:

```
atgtctttt  attccaagca  ggactataat  atggatttag  agctcgacga  gtattataac   60
aagacacttg  ccacagagaa  taatactgct  gccactcgga  attctgattt  cccagtctgg  120
gatgactata  aaagcagtgt  agatgactta  cagtattttc  tgattgggct  ctatacattt  180
gtaagtcttc  ttggctttat  ggggaatcta  cttattttaa  tggctctcat  gaaaaagcgt  240
aatcagaaya  ctacggtaaa  cttcctcata  ggcaatctgg  cctttctga  tatcttggtt  300
gtgctgtttt  gctcacccttt  cacactgacg  tctgtcttgc  tggatcagtg  gatgtttggc  360
aaagtcatgt  gccatattat  gccttttctt  caatgtgtgt  cagttttggt  ttcaacttta  420
attttaatat  caattgccat  tgtcaggtat  catatgataa  aacatcccat  atctaataat  480
```

-continued

```
ttaacagcaa accatggcta ctttctgata gctactgtct ggacactagg ttttgccatc   540
tgttctcccc ttccagtgtt tcacagtctt gtggaacttc aagaaacatt tggttcagca   600
ttgctgagca gcaggtattt atgtgttgag tcatggccat ctgattcata cagaattgcc   660
tttactatct ctttattgct agttcagtat attctgccct tagtttgtct tactgtaagt   720
catacaagtg tctgcagaag tataagctgt ggattgtcca acaaagaaaa cagacttgaa   780
gaaaatgaga tgatcaactt aactcttcat ccatccaaaa agagtgggcc tcaggtgaaa   840
ctctctggca gccataaatg gagttattca ttcatcaaaa aacacagaag aagatatagc   900
aagaagacag catgtgtgtt acctgctcca gaaagacctt ctcaagagaa ccactccaga   960
atacttccag aaaactttgg ctctgtaaga agtcagctct cttcatccag taagttcata  1020
ccaggggtcc ccacttgctt tgagataaaa cctgaagaaa attcagatgt tcatgaattg  1080
agagtaaaac gttctgttac aagaataaaa aagagatctc gaagtgtttt ctacagactg  1140
accatactga tattagtatt tgctgttagt tggatgccac tacacctttt ccatgtggta  1200
actgatttta atgacaatct tatttcaaat aggcatttca agttggtgta ttgcatttgt  1260
catttgttgg gcatgatgtc ctgttgtctt aatccaattc tatatgggtt tcttaataat  1320
ggaattcaga gagacttgca gttcttcttc aacttttgtg atttccggtc tcgggatgat  1380
gattatgaaa caatagccat gtccacgatg cacacagatg tttccaaaac ttctttgaag  1440
caagcaagcc cagtcgcatt taaaaaaatc aacaacaatg atgataatga aaaaatctga  1500
```

Description Of Artificial Sequence:Y5/Y1 CHIMERA

```
Met Ser Phe Tyr Ser Lys Gln Asp Tyr Asn Met Asp Leu Glu Leu Asp
  1               5                  10                  15

Glu Tyr Tyr Asn Lys Thr Leu Ala Thr Glu Asn Asn Thr Ala Ala Thr
             20                  25                  30

Arg Asn Ser Asp Phe Pro Val Trp Asp Asp Tyr Lys Ser Ser Val Asp
         35                  40                  45

Asp Leu Gln Tyr Phe Leu Ile Gly Leu Tyr Thr Phe Val Ser Leu Leu
     50                  55                  60

Gly Phe Met Gly Asn Leu Leu Ile Leu Met Ala Leu Met Lys Lys Arg
 65                  70                  75                  80

Asn Gln Lys Thr Thr Val Asn Phe Leu Ile Gly Asn Leu Ala Phe Ser
                 85                  90                  95

Asp Ile Leu Val Val Leu Phe Cys Ser Pro Phe Thr Leu Thr Ser Val
            100                 105                 110

Leu Leu Asp Gln Trp Met Phe Gly Lys Val Met Cys His Ile Met Pro
        115                 120                 125

Phe Leu Gln Cys Val Ser Val Leu Val Ser Thr Leu Ile Leu Ile Ser
    130                 135                 140

Ile Ala Ile Val Arg Tyr His Met Ile Lys His Pro Ile Ser Asn Asn
145                 150                 155                 160

Leu Thr Ala Asn His Gly Tyr Phe Leu Ile Ala Thr Val Trp Thr Leu
                165                 170                 175

Gly Phe Ala Ile Cys Ser Pro Leu Pro Val Phe His Ser Leu Val Glu
            180                 185                 190

Leu Gln Glu Thr Phe Gly Ser Ala Leu Leu Ser Ser Arg Tyr Leu Cys
        195                 200                 205
```

-continued

```
Val Glu Ser Trp Pro Ser Asp Ser Tyr Arg Ile Ala Phe Thr Ile Ser
    210                 215                 220

Leu Leu Leu Val Gln Tyr Ile Leu Pro Leu Val Cys Leu Thr Val Ser
225             230                 235                     240

His Thr Ser Val Cys Arg Ser Ile Ser Cys Gly Leu Ser Asn Lys Glu
            245                 250                 255

Asn Arg Leu Glu Glu Asn Glu Met Ile Asn Leu Thr Leu His Pro Ser
            260                 265                 270

Lys Lys Ser Gly Pro Gln Val Lys Leu Ser Gly Ser His Lys Trp Ser
        275                 280                 285

Tyr Ser Phe Ile Lys Lys His Arg Arg Arg Tyr Ser Lys Lys Thr Ala
    290                 295                 300

Cys Val Leu Pro Ala Pro Glu Arg Pro Ser Gln Glu Asn His Ser Arg
305             310                 315                     320

Ile Leu Pro Glu Asn Phe Gly Ser Val Arg Ser Gln Leu Ser Ser Ser
            325                 330                 335

Ser Lys Phe Ile Pro Gly Val Pro Thr Cys Phe Glu Ile Lys Pro Glu
            340                 345                 350

Glu Asn Ser Asp Val His Glu Leu Arg Val Lys Arg Ser Val Thr Arg
        355                 360                 365

Ile Lys Lys Arg Ser Arg Ser Val Phe Tyr Arg Leu Thr Ile Leu Ile
    370                 375                 380

Leu Val Phe Ala Val Ser Trp Met Pro Leu His Leu Phe His Val Val
385             390                 395                     400

Thr Asp Phe Asn Asp Asn Leu Ile Ser Asn Arg His Phe Lys Leu Val
            405                 410                 415

Tyr Cys Ile Cys His Leu Leu Gly Met Met Ser Cys Cys Leu Asn Pro
            420                 425                 430

Ile Leu Tyr Gly Phe Leu Asn Asn Gly Ile Gln Arg Asp Leu Gln Phe
        435                 440                 445

Phe Phe Asn Phe Cys Asp Phe Arg Ser Arg Asp Asp Asp Tyr Glu Thr
    450                 455                 460

Ile Ala Met Ser Thr Met His Thr Asp Val Ser Lys Thr Ser Leu Lys
465             470                 475                     480

Gln Ala Ser Pro Val Ala Phe Lys Lys Ile Asn Asn Asn Asp Asp Asn
            485                 490                 495

Glu Lys Ile
```

NPY-5 Ca++ Mobilization Functional Assay

A stable Bowes melanoma cell line was generated expressing functional Y5 receptors useful for the secondary screening of Y5 antagonists using a calcium fluorescence assay. The coding sequence for human Y5 receptor was subcloned into a novel mammalian expression vector called pM². This expression vector has a Harvey murine sarcoma virus long terminal repeat to drive expression of the Y5 structural gene. This plasmid construct was used in transfection experiments with human Bowes melanoma cell line (HMCB; obtained from ATCC, Rockville, Md.), a cell line in which several Gαi-linked receptors are expressed at reasonable levels and are coupled to functional responses. Cells were maintained at 37° C. and 5% $CO_2$ in Eagle's minimum essential medium with 0.1 mM non-essential amino acids, 1.0 mM sodium pyruvate and 25 mM HEPES which was supplemented with 10% fetal bovine serum (pH 7.3). This cell host exhibits low levels of Y1 responses and sites, and no other NPY-induced responses. The Y1 antagonist BIBP3226 at 10 uM completely blocked the endogenous NPY response. A single clonal cell line was isolated and characterized with the agonist peptide NPY. In the presence of 10 uM BIBP3226, NPY stimulated calcium mobilization with an $EC_{50}$ from 9 nM to 54 nM in ten independent studies.

In routine studies, cells were plated onto 96 well plates at 30,000 cells/well for twenty-four hours. The cells were rinsed with buffered saline (consisting of: 115 mM NaCl, 0.96 mM $NaH_2PO_4$, 1 mM $MgSO_4$, 25 mM HEPES, 2 mM $CaCl_2$, 5 mM KCl, 5 mM Glucose, 1 mM Probenecid) and incubated for 1.5 hrs. in the fluorescent $Ca^{2+}$ indicator Fluo-3 AM (10 μM, Teflabs, Austin, Tex.) made in the same buffered saline. Cells were rinsed twice with buffer supplemented with 1 mM carbachol and 10 μM BIBP3226. NPY applied to HMCB Y5 cells produced a concentration dependent increase in intracellular calcium as determined by an increase in fluorescence read on a Fluorometric Imaging Plate Reader (FLIPR, Molecular Devices, Sunnyvale, Calif.). The concentration of NPY used in these experiments was between the $EC_{30}$ and $EC_{50}$ as determined just prior to each experiment. Fluorescence increase in response to NPY in the presence of test compounds was compared to control responses in the same plate and the $IC_{50}$ for each compound was determined by a fit of the data to the logistic equation (Kaleidograph software, Reading Pa.).

Reduction of Food Intake

The utility of the compounds of the instant invention in the reduction of food intake and stimulation of metabolic rate according to the practice of the methods of the invention was demonstrated according to the following protocols.

Rat Food Deprivation Model

Experimentally naive or experienced male Sprague-Dawley rats (Sasco, St. Louis, Mo.) weighing 210–300 g at the beginning of the experiment are used. Animals are triple-housed in stainless steel hanging cages in a temperature (22 C.±2) and humidity (40–70% RH) controlled animal facility with a 12:12 hour light-dark cycle. Food (Standard Rat Chow, PMI Feeds Inc., #5012) and water are available ad libitum. Consumption data are collected while the animals are housed in Nalgene Metabolic cages (Model #650-0100). Food consumption, water consumption, and body weight are measured with an Ohaus Portable Advanced scale (±0.1 g accuracy).

Prior to the day of testing, animals are habituated to the testing apparatus by placing each animal in the Metabolic cage for 1 hour. On the day of the experiment, animals that were food deprived for the previous 24 hours are weighed and assigned to treatment groups. Assignments are made using a quasi-random method utilizing the body weights to assure that the treatment groups have similar average body weight. Animals are administered either vehicle (0.5% MC for oral dosing or 50%/75% PEG for IV dosing) or drug. At that time, the feeding drawer filled with pulverized chow and the filled water bottle are weighed. Following the appropriate pretreatment time (2 hours for PO administration and 15 minutes for IV administration) each animal is weighed and placed in the Metabolic Cage. Following a three-hour test session, animals are removed and body weight obtained. The food and water containers are then weighed and the data recorded.

The means and standard errors of the mean (SEM) for food consumption, water consumption, and body weight change are presented. One-way analysis of variance is used to test for group differences. A significant effect is defined as having a p value of <0.05.

Rat Overnight Feeding Model

The above protocol is used for the overnight feeding model with the following exceptions:

Animals are not habituated.

Animals are not food deprived.

Animals are dosed 2 hours prior to lights off.

All compounds are given PO.

Feces and urine output are also recorded.

The test session begins at lights off (6:30 pm) and ends the following morning, approximately 13 hours later.

Canine Food Intake Studies

Healthy, (1–3 years of age) male and female beagles (Marshall Farms, North Rose, New York, N.Y. 14516) weighing 11–16 kg were employed as test subjects. The dogs were housed individually in standard caging meeting or exceeding the USDA regulations (U.S. Department of Agriculture, Animal Welfare, Final Rules. 9 C.F.R. Parts 1–3, 1995).

In the studies described, dogs received test compound once daily for 4 to 28 days. Test compound was provided as a water-soluble powder. The dosing solution, administered by oral gavage, was a 0.5% methylcellulose vehicle. The dosing solution was prepared at 1 mg/mL activity so that 1 mL was delivered per kg body weight.

The studies consisted of 1–3 groups of animals containing 4–8 dogs. Following a 7-day baseline period (designated as Days-7 to-1), during which time the test animals were evaluated for certain criteria including determination of food intake, body weight and metabolic rate, a 4–28 day evaluation study was effected. On Days 0–3 or 0–27, each dog received the dosing solution administered as a single dose at Time 0 on each dosing day via a feeding tube. This was followed by a 10-mL water rinse to ensure total delivery of dosing solution. Each test animal was permitted ad libitum access to water and IAMS MiniChunks® (The IAMS Company, Dayton, Ohio) dry food each day during the study unless otherwise noted.

Reductions in food intake were quantitated by weighing individual food bowls each day prior to feeding and at the end of each 24-hour consumption period. The difference between these weights represents the amount of food consumed by the dog during the 24 hour consumption period. At the start of each study, there was a seven-day baseline period (designated as Days-7 to-1), during which time the test animals' baseline food intake was evaluated. The difference between the mean amount consumed on days-7 to-1 and the amount consumed following compound administration represents the reduction in food intake attributable to the test compound.

Changes in metabolic rate were quantitated by standard indirect calorimetry using an open circuit calorimeter (Oxymax Deluxe®, Columbus Instruments, Columbus, Ohio). Dogs were fasted for approximately 18 hours prior to test compound administration. Calorimetry sessions were initiated approximately 2 hours after compound administration on selected days of the 4 and 28 day evaluation studies, and lasted for 60–90 minutes. At the start of each study, there was a seven-day baseline period (designated as Days-7 to-1), during which time the test animals baseline metabolic rate was evaluated. The difference between the mean metabolic rate determined on days-7 to-1 and the metabolic rate determined following compound administration represents the increase in metabolic rate attributable to the test compound.

The compounds of general formula I–IV may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I–IV and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I–IV may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

As a consequence of their action in treating pathological conditions the compounds of the present invention possess utility for treatment of household pets, for example companion animals such as dogs and cats. The administration of an active compound of formula I–IV can be effected orally or parenterally. An amount of an active compound of formula I is administered such that an effective dose is received, generally a daily dose which, when administered orally to an animal is usually between 0.01 and 20 mg/kg of body weight, preferably between 0.05 and 10 mg/kg of body weight. Conveniently, the medication can be carried in drinking water so that a therapeutic dosage of the agent is ingested with the daily water supply. The agent can be directly metered into drinking water, preferably in the form of a liquid, water-soluble concentrate (such as an aqueous solution of a water soluble salt).

Conveniently, the active compound can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix With the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Drinking water and feed effective for treating domestic animals are generally prepared by mixing a compound of the invention with a sufficient amount of animal feed to provide from about $10^{-3}$ to 500 ppm of the compound in the feed or water.

The preferred domestic pet feeds usually contain about 1 to 400 grams and preferably 10 to 400 grams of active compound per ton of feed.

In general, parenteral administration involves injection of a sufficient amount of the compounds of the present invention to provide the animal with 0.01 to 20 mg/kg/day of body weight of the active ingredient. The preferred dosage for domestic pets is in the range of from 0.05 to 10 mg/kg/day of body weight of active ingredient.

Experimental Section

Abbreviations: EDC=1-(3-diethylaminopropyl)-3-ethylcarbodiimide hydrochloride; CDI=1,1'-carbonyldiimidazole; DMF=N,N-dimethylformamide.

EXAMPLES

Example 9

4-Dimethylamino-N-(9-ethyl-9H-carbazol-3-yl)-butyramide

To a solution of 3-amino-9-ethylcarbazole (500 mg, 2.38 mol), 3-(dimethylamino)butyric add (438 mg, 2.62 mmol, 1.1 equiv), triethylamine (0.398 mL, 289 mg, 2.85 mmol, 1.2 equiv) and DMAP (145 mg, 0.5 equiv) in $CH_2Cl_2$ (10 mL) was added EDC (500 mg, 2.62 mmol). The resultant solution was maintained at room temperature for 19 hours, and then poured into water and extracted with $CH_2Cl_2$ (2×25 ml). The combined organics were washed with water (1×25 ml), dried over anhydrous $Na_2SO_4$ and concentrated. Purification of the residue by flash column chromatography 10% $MeOH/CH_2Cl_2$ grading to 2% ammonium hydroxide/10% $MeOH/CH_2Cl_2$) provided 4-dimethylamino-N-(9-ethyl-9H-carbazol-3-yl)-butyramide (595 mg, 77%) as a tan foam.

Example 13

N-(9-Ethyl-9H-carbazol-3-yl)-3-piperidin-1-yl-propionamide

Trimethylaluminum (7.1 mL of a 2.0 M solution in hexanes, 14.26 mmol, 3.0 equiv) was added to a solution of 3-amino-9-ethylcarbazole (1.0 g, 4.75 mmol, 1 equiv) in $CH_2Cl_2$ (43 mL). The resultant solution was stirred at room temperature for 30 min, and then ethyl 3-piperidinepropionate (2.85 mL, 2.64 g, 14.26 mmol, 3.0 equiv) was added via syringe. The reaction mixture was heated to 50 ° C. for 17.5 hours and then excess aluminum reagent was quenched by the addition of 1N HCl (10 mL). The reaction mixture was then poured into water (50 mL) and extracted with ethyl acetate (2×50 mL). The combined organics were dried over anhydrous sodium sulfate and concentrated. The residue was purified by flash column chromatography (5% methanol/dichloromethane grading to 10% $MeOH/CH_2Cl_2$) to provide N-(9-ethyl-9H-carbazol-3-yl)-3-piperidin-1-yl-propionamide, which was converted to its HCl salt (1.38 g yellow-brown foam, 69%).

Example 41

N-(9-Isopropyl-9H-carbazol-3-yl)-trifluoroacetamide

Trifluoroacetic anhydride (0.094 mL, 0.668 mmol, 3 equiv) was added to a solution of 3-amino-9-isopropylcarbazole (50 mg, 0.223 mmol 1 equiv), triethylamine (0.186 mL, 135 mg, 6 equiv) and DMAP (5 mg) in $CH_2Cl_2$ (5 mL). The resultant solution was stirred at room temperature for 22 hours and then diluted with ethyl acetate (10 mL). The mixture was washed with saturated aqueous sodium chloride (3×5 mL) and dried over anhydrous sodium sulfate. The residue was purified by rotary chromatography (20% ethyl acetate in hexanes) to provide N-(9-isopropyl-9H-carbazol-3-yl)-trifluoroacetamide (43 mg, 60%) as a pale yellow solid.

Example 44

3-[4-(4-Chloro-phenyl)-4-hydroxy-piperidin-1-yl]-N-(9-ethyl-9H-carbazol-3-yl)-propionamide 4-(4-Chlorophenyl)-4-hydroxypiperidine (229 mg, 1.1 mmol, 1.5 equiv) was added in one portion to a solution of 3-bromo-N-(9-ethyl-9H-carbazol-3-yl)-propionamide (250 mg, 0.72 mmol, 1 equiv) and triethylamine (0.301 mL, 219 mg, 2.2 mmol) in DMF (2 mL). The resultant solution was maintained at room temperature for 21 hours and then diluted with ethyl acetate (25 mL). The mixture was washed with water (25 mL) and saturated aqueous sodium chloride (2×25 mL), dried over anhydrous sodium sulfate and concentrated. The residue was purified by rotary chromatography (5% $MeOH/CH_2Cl_2$) to afford 3-[4-(4-chloro-phenyl)-4-hydroxy-piperidin-1-yl]-N-(9-ethyl-9H-carbazol-3-yl)-propionamide (278 mg, 81%) as a white solid.

Example 45

4-Dimethylamino-N-(9-ethyl-9H-carbazol-3-yl)-N-methyl-butyramide

Sodium hydride (8 mg of a 60% suspension in mineral oil, 4 mg, 0.19 mmol, 1.2 equiv) was added to a solution of 4-dimethylamino-N-(9-ethyl-9H-carbazol-3-yl)-butyramide (50 mg, 0.15 mmol, 1 equiv) in DMF (0.3 mL). The resultant suspension was stirred at room temperature for 1 hour, and then iodomethane (0.012 mL, 27 mg, 0.19 mmol, 1.25 equiv) was added via syringe. After an additional 5 hours at room temperature, the reaction mixture was diluted with water (5 mL) and extracted with ethyl acetate (3×5 mL). The combined extracts were washed with water (1×10 mL) and brine (1×10 mL), dried over anhydrous sodium sulfate and concentrated. The residue was purified by rotary chromatography ($CH_2Cl_2$ grading to 2% ammonium hydroxide in 5% $MeOH/CH_2Cl_2$) to provide 4-dimethylamino-N-(9-ethyl-9H-carbazol-3-yl)-N-methyl-butyramide (3 mg, 5%) as a yellow oil.

Example 68

N-(9-Ethyl-9H-carbazol-3-yl)-2-(6-amino-3-aza-bicyclo[3.1.0]hex-3-yl)-acetamide 3-[(9-Ethyl-9H-carbazol-3-ylcarbamoyl)-methyl]-3-aza-bicyclo[3.1.0]hex-6-yl}-carbamic acid tert-butyl ester was synthesized similarly to example 44, substituting 3-aza-bicyclo[3.1.0]hex-6-yl)-carbamic acid tert-butyl ester for 4-(4-Chlorophenyl)-4-hydroxypiperidine and substituting the compound of example 19 for the compound of example 40. A solution of {3-[(9-ethyl-9H-carbazol-3-ylcarbamoyl)-methyl]-3-aza-bicyclo[3.1.0]hex-6-yl}-carbamic acid tert-butyl ester (4.6 mmol) in 1:1 4 M HCl/dioxane (25 mL) was stirred at room temperature for 16 hours. The reaction mixture was then concentrated, and the residue was concentrated from diethyl ether (2×25 mL). The pale yellow foam remaining (723 mg, 37%) was N-(9-ethyl-9H-carbazol-3-yl)-2-(6-amino-3-aza-bicyclo[3.1.0]hex-3-yl)-acetamide.

Example 70

N-(9-Ethyl-9H-carbazol-3-yl)-2-(6-isobutylamino-3-aza-bicyclo[3.1.0]hex-3-yl)-acetamide A solution of 2-(6-Amino-3-aza-bicyclo[3.1.0]hex-3-yl)-N-(9-ethyl-9H-carbazol-3-yl)-acetamide hydrochloride salt (100 mg, 0.26 mmol) in 1,2-dichloroethane (3 ml) was treated with $NaBH(OAc)_3$ (82.3 mg, 0.39 mmol), glacial acetic acid (15 μl, 0.26 mmol), $Et_3N$ (28 mg, 0.29 mmol) and isobutyaldehyde (24 μl, 0.26 mmol) and the reaction mixture stirred at room temperature for several days. The reaction was then diluted with EtOAc and washed with 1N NaOH, brine, the organic layer dried ($MgSO_4$) and concentrated to afford the crude product. Chromatographic purification (silica, 5% $MeOH/CH_2Cl_2$) afforded the desired product as a white solid, which was converted to the dihydrochloride salt ($Et_2O$/ethereal HCl; 106 mg, 85% yield). MS m/z @ 405 (m+1).

Example 71

N-3-Bromo-(9-ethyl-9H-carbazol-6-yl)-trifluoroacetamide

To a solution of N-(9-ethyl-9H-carbazol-6-yl)-trifluoroacetamide (306 mg, 1 mmol) in $CH_2Cl_2$ (5 ml) at room temperature was added bromine (57 μl, 1.1 mmol), and after stirring 10 minutes the reaction mixture washed with 10% aq. sodium thiosulfate and brine, the organic layer dried ($Na_2SO_4$) and concentrated to afford the crude product. Chromatographic purification (silica, 10% EtOAc/Hex) afforded the desired product as a yellow solid (200 mg, 52% yield). MS m/z @ 383, 385 (m−1, AP-).

9-Isopropyl-3-nitro-9H-carbazole

A solution of 9-Isopropyl-9H-carbazole (Acros, 1.5 9, 7.2 mmol) in AcOH (50 ml) was treated dropwise with a solution of nitric acid (3.35 ml) in AcOH (10 mL) over 30 minutes. When the reaction was complete the mixture was poured into water and stirred for 15 minutes, then the solid filtered and washed with $Et_2O$ to afford the desired product as a solid (1.6 g, 87%).

9-Isopropyl-3-amino-9H-carbazole

To a solution of 9-Isopropyl-3-nitro-9H-carbazole(1.5 g, 5.89 mmol) in EtOH (100 ml) was added 10% Pd-C (150 mg) and the reaction mixture was hydrogenated with a Parr hydrogenation apparatus at 45 psi $H_2$ pressure for 3 hours. The reaction mixture was filtered and the filtrate concentrated in vacuo to afford the desired product as a solid (1.3 g, 87%).

9-Ethyl-9H-carbazole-3-carboxylic acid

To a solution of 9-Ethyl-9H-carbazole-3-carbaldehyde (Aldrich, 5.0 g, 22.39 mmol) in acetone (100 ml) at 70° C. under nitrogen was added dropwise a solution of $KMnO_4$ (4.74 g, 30.00 mmol) in $H_2O$ (100 ml) slowly over 1 hour. When the reaction was complete the reaction mixture was filtered through celite, the celite pad washed with $H_2O$/acetone, and the filtrate washed with ether. The aqueous layer was then acidified to pH 2 with aqueous HCl, and the white precipitate filtered and dried under vacuum to afford the desired product (4.05 g, 76% yield). MS m/z @ 240 (m+1).

Example 72

N-(9-Ethyl-6-formyl-9H-carbazol-3-yl)-acetamide

To a solution of N-3-Bromo-(9-ethyl-9H-carbazol-6-yl)-trifluoroacetamide (200 mg, 0.519 mmol) in THF (4 ml) at −78° C. was added n-butyllithium (714 μl, 1.142 mmol) slowly, and after 10 minutes the reaction mixture was quenched with dry DMF (500 μl) and the cooling bath removed. After stirring an additional 20 minutes the reaction mixture was diluted with $H_2O$/EtOAc and the organic layer washed with brine (2×), dried ($Na_2SO_4$) and concentrated to afford the crude product as a white solid (167 mg) Recrystallization from acetone afforded the pure product (50 mg, 29% yield). MS m/z @ 333 (m−1, AP-).

Example 73

N-(9-Ethyl-6-hydroxymethyl-9H-carbazol-3-yl)-acetamide

To a solution of N-(9-Ethyl-6-formyl-9H-carbazol-3-yl)-acetamide (50 mg, 0.150 mmol) in EtOH (5 ml) at 0° C. was added $NaBH_4$ (8.5 mg, 0.225 mmol), and after 10 minutes the cooling bath was removed. After 1 hour additional $NaBH_4$ (2 mg) was added, and after stirring 90 minutes water was added, the EtOH removed in vacuo, and the aqueous layer extracted with $CH_2Cl_2$. The organic layer was dried ($Na_2SO_4$) and concentrated to afford the crude product. Chromatographic purification (silica, 50% EtOAc/Hex) afforded the product as a solid (28 mg, 56% yield). MS m/z @ 337 (m+1).

Example 74

N-(9-Ethyl-9H-carbazol-3-yl)-methanesulfonamide

To a solution of 9-Ethyl-9H-carbazol-3-ylamine (210 mg, 1 mmol) and pyridine (105 μl, 1.3 mmol) in $CH_2Cl_2$ (8 ml)

at room temperature was added methanesulfonyl chloride (85 µl, 1.1 mmol). After stirring overnight the reaction mixture was diluted with $CH_2Cl_2$ and washed with saturated aq. $NaHCO_3$ and brine, then the organic layer dried ($Na_2SO_4$) and concentrated to afford the crude product. Chromatographic purification (silica, $CH_2Cl_2$) afforded the desired product as a pale yellow solid (203 mg, 70% yield).

Example 75

N-[6-(3,4-Dihydro-1H-isoquinolin-2-ylmethyl)-9-ethyl-9H-carbazol-3-yl]-2,2,2-trifluoro-acetamide To a solution of N-(9-Ethyl-6-formyl-9H-carbazol-3-yl)-acetamide (100 mg, 0.299 mmol) in 1,2-dichloroethane (3 ml) at room temperature was added AcOH (17 µL, 0.299 mmol) followed by 1,2,3,4-tetrahydroisoquinoline (45 µL, 0.359 mmol) and sodium triacetoxyborohydride (88.7 mg, 0.418 mmol). After several hours a second aliquot of sodium triacetoxyborohydride (31 mg) was added and the reaction mixture stirred overnight. The reaction mixture was then diluted with saturated aq. $NaHCO_3$ and extracted with $CH_2Cl_2$, and the organic layer dried ($Na_2SO_4$) and concentrated to afford the crude product. Chromatographic purification (silica, 3% $MeOH/CH_2Cl_2$) afforded the product, which was converted to the HCl salt (110 mg, 75% yield). MS m/z @ 452 (m+1).

Example 77

N-(9-Ethyl-9H-carbazol-3-yl)-2-pyridin-3-yl-N-methylacetamide

To a suspension of N-(9-Ethyl-9H-carbazol-3-yl)-2-pyridin-3-yl-acetamide (329 mg, 0.899 mmol) in THF at 0° C. was added NaH (60% oil dispersion, 86 mg, 2.158 mmol), then the cooling bath removed. After stirring an additional 25 minutes methyl iodide (67 µl, 1.08 mmol) was added, and the reaction mixture stirred overnight. A portion of DMF (4 ml) was then added and stirring continued for several hours. The reaction mixture was then diluted with EtOAc and the organic layer washed with saturated aq. $NaHCO_3$, $H_2O$, and brine, dried ($Na_2SO_4$), and concentrated to afford the crude product as a brown oil. Chromatographic purification (silica, 10% $MeOH/CH_2Cl_2$) afforded the desired product (7 mg, 2.2% yield). MS m/z @ 344 (m+1).

Example 81

9-Ethyl-9H-carbazole-3-carboxylic acid benzylamide

To a suspension of 9-Ethyl-9H-carbazole-3-carboxylic acid (75 mg, 0.313 mmol) in $CH_2Cl_2$ (1 ml) at room temperature was added CDI (56 mg, 0.344 mmol) ) in $CH_2Cl_2$ (1 ml), and after stirring for 30 minutes benzylamine (38 µl, 0. 344 mmol) was added. When the reaction was complete the reaction mixture was directly loaded onto a silica column and eluted with $CH_2Cl_2$ to afforded the desired product as a white foam (86 mg, 84% yield). MS m/z @ 329 (m+1).

Example 88

9-Ethyl-9H-carbazole-3-carboxylic acid {2-[(thiazol-2-ylmethyl)-amino]-ethyl}-amide $N^1$-Benzyl-ethane-1,2-diamine (6.0 g, 25.1 mmol) was coupled with 9-Ethyl-9H-carbazole-3-carboxylic acid as described in example 81 to afford, after chromatographic purification (silica; 3% $MeOH/CH_2Cl_2$) 9-Ethyl-9H-carbazole-3-carboxylic acid (2-benzylamino-ethyl)-amide (4.5 g, 48%) (MS m/z @ 372 (m+1). This material was subjected to catalytic hydrogenation ((10%Pd—C/$H_2$ @ 50 psi) in EtOH/AcOH to afford 9-Ethyl-9H-carbazole-3-carboxylic acid (2-amino-ethyl)-amide (3.16 g, 92%) as a white solid MS m/z @ 282 (m+1). This material was reductively aminated using sodium triacetoxyborohydride and thiazole-2-carbaldehyde similarly to conditions described for example 75 to afford the title compound (350 mg, 65%). MS m/z @ 379 (m+1).

Example 95

(S)-2-(3-Diethylamino-2-hydroxy-propylamino)-N-(9-ethyl-9H-carbazol-3-yl)-acetamide To a solution of 3-amino-9-ethylcarbazole (8.1 g, 38 mmol), tert-butoxycarbonylamino-acetic acid (6.7 g, 38 mmol), and N,N-dimethylaminopyridine (5.7 g, 46 mmol) in $CH_2Cl_2$ (125 mL) was added EDC (5.5 g, 46 mmol). The resultant solution was stirred at room temperature for 2 days, and then diluted with ethyl acetate (500 mL) and washed with aqueous 1 M HCl (2×100 mL), water (100 mL), saturated aqueous $NaHCO_3$ (100 mL), and then brine (100 mL). The organic layer was then dried ($Na_2SO_4$), concentrated under reduced pressure, and then flash chromatographed (silica, 1:39 to 1:19 to 1:9 ethyl acetate/$CH_2Cl_2$) to afford [(9-ethyl-9H-carbazol-3-ylcarbamoyl)-methyl]-carbamic acid tert-butyl ester (9.1 g, 65%) as a brown foam. MS m/z @ 368 (M+1).

The [(9-ethyl-9H-carbazol-3-ylcarbamoyl)-methyl]-carbamic acid tert-butyl ester (9.1 g, 25 mmol) was stirred for 1 hour in 1:1 concentrated aqueous HCl/ethanol to give a gray solid that was concentrated under reduced pressure. The residue was then extracted from saturated aqueous $Na_2CO_3$ with $CH_2Cl_2$, the combined organic layers were dried ($Na_2SO_4$) and then concentrated under reduced pressure to afford 2-amino-N-(9-ethyl-9H-carbazol-3-yl)-acetamide (6.1 g, 93%) as an off-white solid. MS m/z @ 268 (M+1).

To a solution of 2-amino-N-(9-ethyl-9H-carbazol-3-yl)-acetamide (6.1 g, 23 mmol) and triethylamine (6.3 mL, 45 mmol) in DMF (50 mL) was added a solution of (R)-(-)-glycidyl nosylate (5.9 g, 23 mmol) in DMF (20 mL). The resultant solution was stirred two days under nitrogen to form (S)-N-(9-Ethyl-9H-carbazol-3-yl)-2-(oxiranylmethyl-amino)-acetamide, which was then directly treated with diethyl amine (23 mL, 227 mmol) and methanol (100 mL). The mixture was stirred an additional two days, and then concentrated under reduced pressure to remove the methanol. The concentrated reaction was diluted with ethyl acetate (1 L) and washed with saturated aqueous $Na_2CO_3$ (1 L), water (2×500 mL), and then brine (250 mL). The organic solution was then dried ($Na_2SO_4$), concentrated under reduced pressure, and flash chromatographed (10:3:1 to 7:3:1 hexanes/diethylamine/acetonitrile) to give the title compound (4.4 g, 49%) as a brown oil which was converted to the dihydrochloride salt (methanol, ethereal HCl). The salt was then re-pulped from refluxing 2:1 ether/methanol to afford the dihydrochloride salt of the title compound as a colorless solid (3.5 g, 33%). MS m/z @ 397 (M+1).

Example 97

(S)-N-(6-tert-Butyl-9-ethyl-9H-carbazol-3-yl)-2-(3-diethylamino-2-hydroxy-propylamino)-acetamide The [(9-ethyl-9H-carbazol-3-ylcarbamoyl)-methyl]-carbamic acid tert-butyl ester prepared in Example 95 (4.7 g, 13 mmol) was stirred for 1 hour in 1:1 CH$_2$Cl$_2$/ trifluoroacetic acid (TFA) and then concentrated under reduced pressure to give the di-TFA salts of 2-amino-N-(9-ethyl-9H-carbazol-3-yl)-acetamide and 2-amino-N-(6-tert-butyl-9-ethyl-9H-carbazol-3-yl)-acetamide in a 5:1 ratio (6.2 g, quantitative) as a gray solid. MS m/z @ 268 (M+1).

To a solution of the above product (5.3 g, 11 mmol) and triethylamine (7 mL, 50 mmol) in DMF (30 mL) was added a solution of (R)-(−)-glycidyl nosylate (2.6 g, 10 mmol). The resultant solution was stirred 21 hours under nitrogen, and then diethylamine (30 mL, 290 mmol) and methanol (70 mL) were added. The mixture was stirred an additional four days, and then concentrated under reduced pressure to remove the methanol. The concentrated reaction was diluted with ethyl acetate (1 L) and washed with saturated aqueous Na$_2$CO$_3$, water (2×), and then brine. The organic solution was then dried (Na$_2$SO$_4$), concentrated under reduced pressure, and flash chromatographed (0.1:1:99 to 0.1:1:49 to 0.1:1:24 to 0.1:1:12 to 0.1:1:9 ammonium hydroxide/ methanol/CH$_2$Cl$_2$). The isolated material was then rechromatographed (10:3:1 to 7:3:1 hexanes/diethylamine/ acetonitrile) to give the title compound (0.26 g, 6%) as a colorless oil (MS m/z @ 453 (M+1)), followed by the product of Example 95 (0.94 g, 23%).

| Example | Method of Synthesis |
|---|---|
| 1 | Synthesized similarly to example 9, substituting 2-(dimethylamino)acetic acid for 3-(dimethylamino)butyric acid |
| 2 | Synthesized similarly to example 9, substituting 3-(diethylamino)propionic acid for 3-(dimethylamino)butyric acid |
| 3 | Synthesized similarly to example 9, substituting 2-fluorobenzoic acid for 3-(dimethylamino)butyric acid |
| 4 | Synthesized similarly to example 9, substituting 2-pyridin-2-yl-thiazole-4-carboxylic acid for 3-(dimethylamino)butyric acid |
| 5 | Synthesized similarly to example 9, substituting 2-(2-pyridyl)acetic acid for 3-(dimethylamino)butyric add |
| 6 | Synthesized similarly to example 9, substituting 2-(3-pyridyl)acetic acid for 3-(dimethylamino)butyric acid |
| 7 | Synthesized similarly to example 9, substituting isonicotinic acid for 3-(dimethylamino)butyric acid |
| 8 | Synthesized similarly to example 9, substituting 1H-Indole-2-carboxylic acid for 3-(dimethylamino)butyric acid |
| 9 | see experimental section |
| 10 | Synthesized similarly to example 9, substituting 2-(4-pyridyl)acetic acid for 3-(dimethylamino)butyric add |
| 11 | Synthesized similarly to example 13, substituting ethyl 1-piperidineacetate for ethyl 1-piperidinepropionate |
| 12 | Synthesized similarly to example 13, substituting ethyl 3-morpholin-4-yl-propionate for ethyl 1-piperidinepropionate |
| 13 | see experimental section |
| 14 | Synthesized similarly to example 9, substituting hydroxydiphenyl acetic acid for 3-(dimethylamino)butyric acid |
| 15 | Synthesized similarly to example 9, substituting 2-hydroxy-2-methyl-propionic acid for 3-(dimethylamino)butyric acid |
| 16 | Synthesized similarly to example 9, substituting 2-hydroxy-2-methyl-butyric add for 3-(dimethylamino)butyric acid |
| 17 | Synthesized similarly to example 9, substituting 2-hydroxy-2-phenyl-propionic acid for 3-(dimethylamino)butyric acid |
| 18 | Synthesized similarly to example 9, substituting (R)-2-hydroxy-2-phenyl-propionic acid for 3-(dimethylamino)butyric acid |
| 19 | Synthesized similarly to example 9, substituting 2-bromoacetic acid for 3-(dimethylamino)butyric acid |
| 20 | Synthesized similarly to example 9, substituting 2-(dimethylamino)propionic acid for 3-(dimethylamino)butyric acid |
| 21 | Synthesized similarly to example 44, substituting [1,2,4]triazine for 4-(4-Chlorophenyl)-4-hydroxypiperidine and substituting compound of example 19 for example 40 |
| 22 | Synthesized similarly to example 44, substituting N-methyl piperazine for 4-(4-Chlorophenyl)4-hydroxypiperidine and substituting compound of example 19 for example 40 |
| 23 | Synthesized similarly to example 44, substituting Bis-(2-hydroxyethyl)amine for 4-(4-Chlorophenyl)A-hydroxypiperidine and substituting compound of example 19 for example 40 |
| 24 | Synthesized similarly to example 44, substituting pyrrolidine for 4-(4-Chlorophenyl)A-hydroxypiperidine and substituting compound of example 19 for example 40 |
| 25 | Synthesized similarly to example 44, substituting benzylamine for 4-(4-Chlorophenyl)4-hydroxypiperidine and substituting compound of example 19 for example 40 |
| 26 | Synthesized similarly to example 9, substituting 3-(4-phenyl-piperidin-1-yl)-propionic acid for 3-(dimethylamino)butyric acid |
| 27 | Synthesized similarly to example 9, substituting 3-(3,4-Dihydro-1H-isoquinolin-2-yl) propionic acid for 3-(dimethylamino)butyric acid |
| 28 | Synthesized similarly to example 9, substituting 3-(2,5-Dihydro-pyrrol-1-yl) propionic acid for 3-(dimethylamino)butyric acid |
| 29 | Synthesized similarly to example 9, substituting 3-indol-1-yl-propionic acid for 3-(dimethylamino)butyric acid |

-continued

| Example | Method of Synthesis |
|---|---|
| 30 | Synthesized similarly to example 9, substituting 3-diphenylaminopropionic acid for 3-(dimethylamino)butyric acid |
| 31 | Synthesized similarly to example 9, substituting 3-(5-Chloro-quinolin-8-yloxy)-propionic acid for 3-(dimethylamino)butyric acid |
| 32 | Synthesized similarly to example 9, substituting 3-Carbazol-9-yl propionic acid for 3-(dimethylamino)butyric acid |
| 33 | Synthesized similarly to example 9, substituting 3-(4-piperidin-1-ylmethyl-phenoxy)-propionic acid for 3-(dimethylamino)butyric acid |
| 34 | Synthesized similarly to example 9, substituting 3-[methyl-(1,2,3,4-tetrahydro-naphthalen-2-yl)-amino]-propionic acid for 3-(dimethylamino)butyric acid |
| 35 | Synthesized similarly to example 9, substituting 3-(quinolin-7-yloxy)-propionic acid for 3-(dimethylamino)butyric acid |
| 36 | Synthesized similarly to example 13, substituting ethyl 3-pyrrolidin-1-yl-propionate for ethyl 1-piperidinepropionate |
| 37 | Synthesized similarly to example 44, substituting 2-Bis-(2-hydroxyethyl)-amine for 4-(4-Chlorophenyl)-4-hydroxypiperidine and substituting compound of example 19 for example 40 |
| 38 | Synthesized similarly to example 44, substituting compound of example 19 for example 40 |
| 39 | Synthesized similarly to example 44, substituting 4-hydroxy-4-phenylpiperidine for 4-(4-Chlorophenyl)A-hydroxypiperidine and substituting compound of example 19 for example 40 |
| 40 | Synthesized similarly to example 9, substituting 3-bromopropionic acid for 3-(dimethylamino)butyric acid |
| 41 | see experimental section |
| 42 | Synthesized similarly to example 9, substituting 3-(4-phenylpiperidin-1-yl)-propionic acid for 3-(dimethylamino)butyric acid |
| 43 | Synthesized similarity to example 44, substituting 4-hydroxy-4-phenylpiperidine for 4-(4-Chlorophenyl)4-hydroxypiperidine |
| 44 | see experimental section |
| 45 | see experimental section |
| 46 | Synthesized similarly to example 44, substituting [1,4']Bipiperidine for 4-(4-Chlorophenyl)4-hydroxypiperidine |
| 47 | Synthesized similarly to example 44, substituting 1-phenylpiperazine for 4-(4-Chlorophenyl)-4-hydroxypiperidine |
| 48 | Synthesized similarly to example 44, substituting 4-benzyl-piperidine for 4-(4-Chlorophenyl)4-hydroxypiperidine |
| 49 | Synthesized similarly to example 44, substituting 4-dimethylamino-piperidine for 4-(4-Chlorophenyl)-4-hydroxypiperidine |
| 50 | Synthesized similarly to example 44, substituting 4-dimethylaminoethyl-piperidine for 4-(4-Chlorophenyl)-4-hydroxypiperidine |
| 51 | Synthesized similarly to example 41, substituting 3-amino-9-methylcarbazole for 3-amino-9-isopropylcarbazole |
| 52 | Synthesized similarly to example 9, substituting 1-hydroxy-cyclopropanecarboxylic acid for 3-(dimethylamino)butyric acid |
| 53 | Synthesized similarly to example 44, substituting 4-cyano-4-phenyl-piperidine for 4-(4-Chlorophenyl)A-hydroxypiperidine |
| 54 | Synthesized similarly to example 44, substituting 4-chlorobenzylamine for 4-(4-Chlorophenyl)-4-hydroxypiperidine and substituting compound of example 19 for example 40 |
| 55 | Synthesized similarly to example 44, substituting 4-phenylpiperidine for 4-(4-Chlorophenyl)-4-hydroxypiperidine and substituting compound of example 19 for example 40 |
| 56 | Synthesized similarly to example 44, substituting 4-(4-fluoro)phenylpiperazine for 4-(4-Chlorophenyl)-4-hydroxypiperidine and substituting compound of example 19 for example 40 |
| 57 | Synthesized similarly to example 44, substituting 4-pyridin-2-yl-piperazine for 4-(4-Chlorophenyl)-4-hydroxypiperidine and substituting compound of example 19 for example 40 |
| 58 | Synthesized similarly to example 44, substituting 4-pyridin-2-yl-piperazine for 4-(4-Chlorophenyl)-4-hydroxypiperidine |
| 59 | Synthesized similarly to example 44, substituting 4-(4-fluoro)-phenylpiperazine for 4-(4-Chlorophenyl)-4-hydroxypiperidine |
| 60 | Synthesized similarly to example 44, substituting 4-fluorobenzylamine for 4-(4-Chlorophenyl)-4-hydroxypiperidine and substituting compound of example 19 for example 40 |
| 61 | Synthesized similarly to example 44, substituting (R)-α-methyl benzylamine for 4-(4-Chlorophenyl)4-hydroxypiperidine and substituting compound of example 19 for example 40 |
| 62 | Synthesized similarly to example 44, substituting (R)-α-methyl-4-chloro-benzylamine for 4-(4-Chlorophenyl)-4-hydroxypiperidine and substituting compound of example 19 for example 40 |
| 63 | Synthesized similarly to example 13, substituting ethyl 3-pyrrolidin-1-yl-propionate for ethyl 1-piperidinepropionate, and using 3-amino-9-isopropyl carbazole instead of 3-amino-9-ethyl carbazole |

-continued

| Example | Method of Synthesis |
|---|---|
| 64 | Synthesized similarly to example 44, substituting 3-diethylamino-2-hydroxy-propylamine for 4-(4-Chlorophenyl)-4-hydroxypiperidine and substituting compound of example 19 for example 40 |
| 65 | Synthesized similarly to example 44, substituting benzylisopropylamine for 4-(4-Chlorophenyl)-4-hydroxypiperidine and substituting compound of example 19 for example 40 |
| 66 | Synthesized similarly to example 44, substituting 4-pyrrolidin-1-yl-piperidine for 4-(4-Chlorophenyl)-4-hydroxypiperidine and substituting compound of example 19 for example 40 |
| 67 | Synthesized similarly to example 70, substituting acetone for isobutyaldehyde |
| 68 | see experimental section |
| 69 | Synthesized similarly to example 70, substituting benzaldehyde for isobutyaldehyde |
| 70 | see experimental section |
| 71 | see experimental section |
| 72 | see experimental section |
| 73 | see experimental section |
| 74 | see experimental section |
| 75 | see experimental section |
| 76 | Synthesized similarly to example 74, substituting chloromethanesulfonyl chloride for methanesulfonyl chloride |
| 77 | see experimental section |
| 78 | Synthesized similarly to example 81, substituting pyridin-3-ylmethylamine for benzylamine |
| 79 | Synthesized similarly to example 81, substituting 4-hydroxy-4-phenylpiperidine for benzylamine |
| 80 | Synthesized similarly to example 81, substituting 2-benzylaminoethylamine for benzylamine |
| 81 | see experimental |
| 82 | Synthesized similarly to example 81, substituting 3-morpholin-4-yl-propylamine for benzylamine |
| 83 | Synthesized similarly to example 81, substituting 1-benzyl-pyrrolidin-3-yl-amine for benzylamine |
| 84 | Synthesized similarly to example 81, substituting 2-isopropylamino-ethylamine for benzylamine |
| 85 | Synthesized similarly to example 81, substituting 2-hydroxyethylamine for benzylamine |
| 86 | Synthesized similarly to example 88, substituting Pyridine-4-carbaldehyde for thiazole-2-carbaldehyde |
| 87 | Synthesized similarly to example 88, substituting 1-Methyl-1H-indole-3-carbaldehyde for thiazole-2-carbaldehyde |
| 88 | see experimental |
| 89 | Synthesized similarly to example 88, substituting Quinoline-2-carbaldehyde for thiazole-2-carbaldehyde |
| 90 | Synthesized similarly to example 88, substituting Quinoline-2-carbaldehyde for thiazole-2-carbaldehyde |
| 91 | Synthesized similarly to example 81, substituting 2-phenylethylamine for benzylamine |
| 92 | Synthesized similarly to example 81, substituting 3-phenylpropylamine for benzylamine |
| 93 | Synthesized similarly to example 81, substituting N1,N1-Diisopropyl-ethane-1,2-diamine for benzylamine |
| 94 | Synthesized similarly to example 81, substituting 3-(2-Methyl-piperidin-1-yl)-propylamine for benzylamine |
| 95 | see experimental section |
| 96 | Synthesized similarly to example 95, substituting (S)-(+)-glycidyl nosylate for (R)-(−)-glycidyl nosylate |
| 97 | see experimental section |

TABLE
Carbazoles with Ki Values <1 uM NPY-5 Binding and Mass Spectrometry Data.
| Example | Structure | Name | Mass Spec Data m/z[1] |
|---|---|---|---|
| 1 | 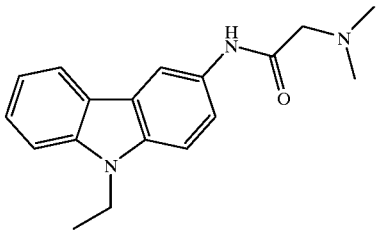 | 2-Dimethylamino-N-(9-ethyl-9H-carbazol-3-yl)-acetamide | 296 |
| 2 | 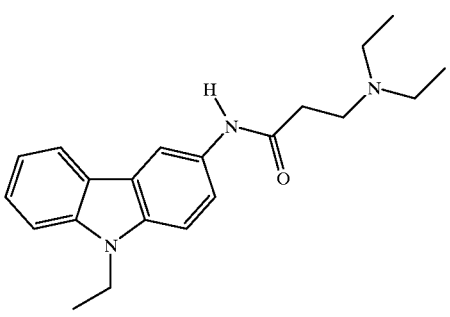 | 3-Diethylamino-N-(9-ethyl-9H-carbazol-3-yl)-propionamide | 338 |
| 3 | 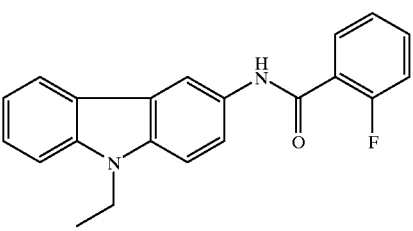 | N-(9-Ethyl-9H-carbazol-3-yl)-2-fluoro-benzamide | 333 |
| 4 | 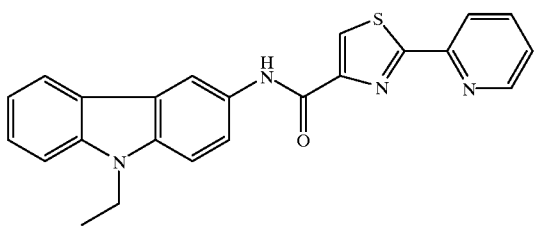 | 2-Pyridin-2-yl-thiazole-4-carboxylic acid (9-ethyl-9H-carbazol-3-yl)-amide | 399 |
| 5 | 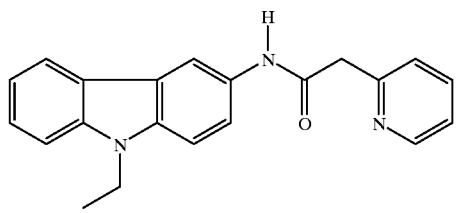 | N-(9-Ethyl-9H-carbazol-3-yl)-2-pyridin-2-yl-acetamide | 330 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 6 | 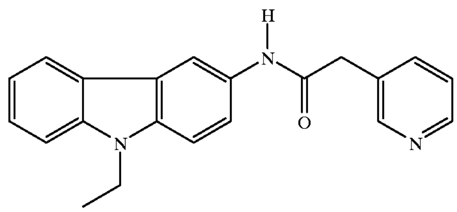 | N-(9-Ethyl-9H-carbazol-3-yl)-2-pyridin-3-yl-acetamide | 330 |
| 7 | 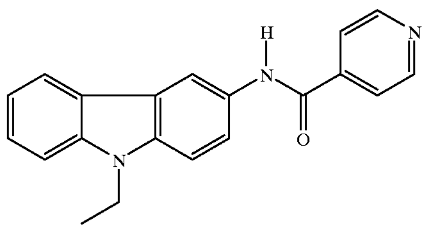 | N-(9-Ethyl-9H-carbazol-3-yl)-isonicotinamide | 316 |
| 8 | 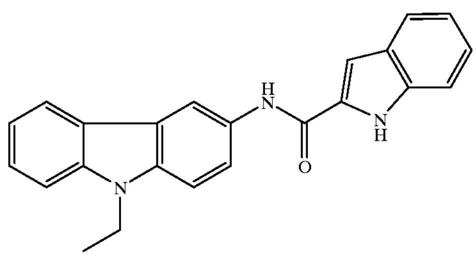 | 1H-Indole-2-carboxylic acid (9-ethyl-9H-carbazol-3-yl)-amide | 354 |
| 9 | 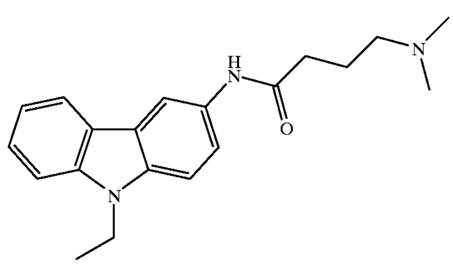 | 4-Dimethylamino-N-(9-ethyl-9H-carbazol-3-yl)-butyramide | 324 |
| 10 | 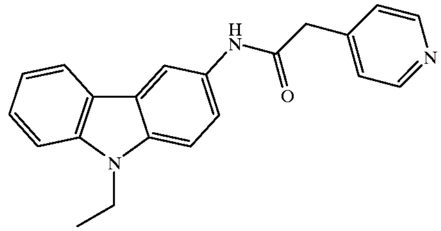 | N-(9-Ethyl-9H-carbazol-3-yl)-2-pyridin-4-yl-acetamide | 330 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 11 | 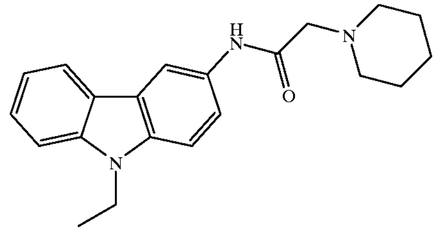 | N-(9-Ethyl-9H-carbazol-3-yl)-2-piperidin-1-yl-acetamide | 336 |
| 12 | 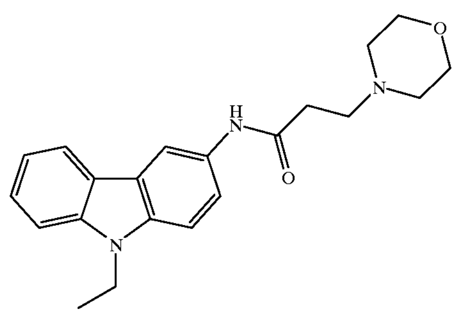 | N-(9-Ethyl-9H-carbazol-3-yl)-3-morpholin-4-yl-propionamide | 352 |
| 13 | 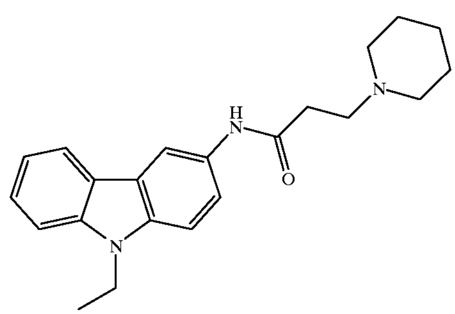 | N-(9-Ethyl-9H-carbazol-3-yl)-3-piperidin-1-yl-propionamide | 350 |
| 14 | 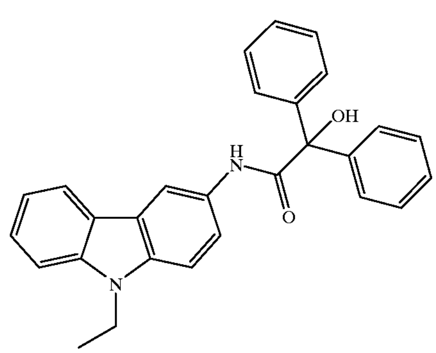 | N-(9-Ethyl-9H-carbazol-3-yl)-2-hydroxy-2,2-diphenyl-acetamide | 419[2] (M$^+$ − H) |

TABLE-continued

Carbazoles with Ki Values <1 uM NPY-5 Binding and Mass Spectrometry Data.

| Example | Structure | Name | Mass Spec Data m/z[1] |
|---|---|---|---|
| 15 | 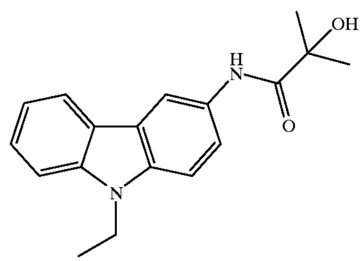 | N-(9-Ethyl-9H-carbazol-3-yl)-2-hydroxy-2-methyl-propionamide | 297 |
| 16 | 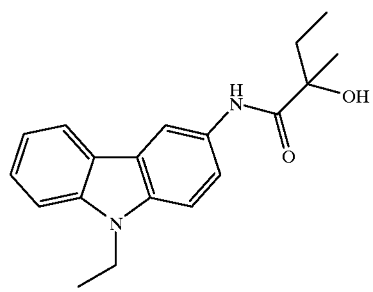 | N-(9-Ethyl-9H-carbazol-3-yl)-2-hydroxy-2-methyl-butyramide | 311 |
| 17 | 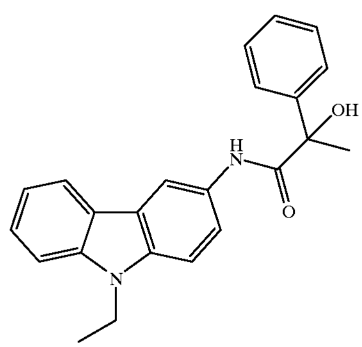 | N-(9-Ethyl-9H-carbazol-3-yl)-2-hydroxy-2-phenyl-propionamide | 359 |
| 18 | 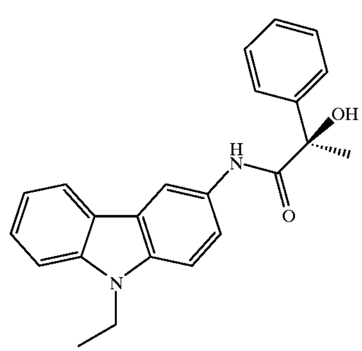 | (R)-N-(9-Ethyl-9H-carbazol-3-yl)-2-hydroxy-2-phenyl-propionamide | 359 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 19 | 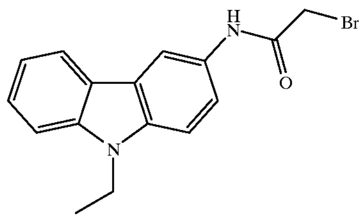 | 2-Bromo-N-(9-ethyl-9H-carbazol-3-yl)-acetamide | 331 |
| 20 | 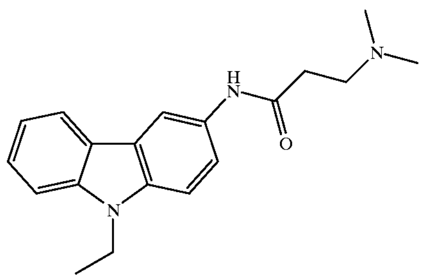 | 3-Dimethylamino-N-(9-ethyl-9H-carbazol-3-yl)-propionamide | 310 |
| 21 | 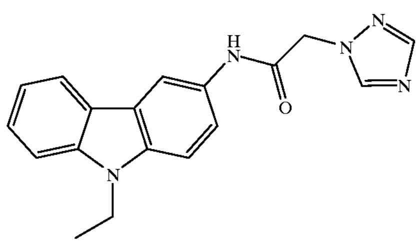 | N-(9-Ethyl-9H-carbazol-3-yl)-2-[1,2,4]triazol-1-yl-acetamide | 320 |
| 22 | 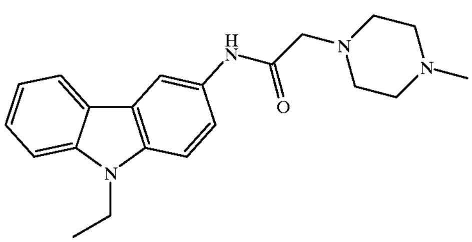 | N-(9-Ethyl-9H-carbazol-3-yl)-2-(4-methyl-piperazin-1-yl)-acetamide | 351 |
| 23 | 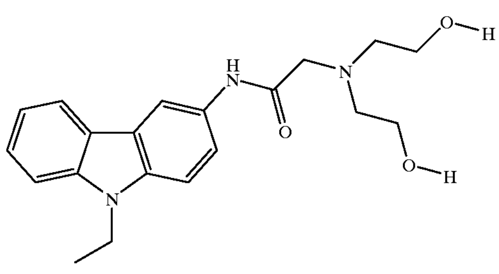 | 2-[Bis-(2-hydroxy-ethyl)-amino]-N-(9-ethyl-9H-carbazol-3-yl)-acetamide | 356 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 24 | 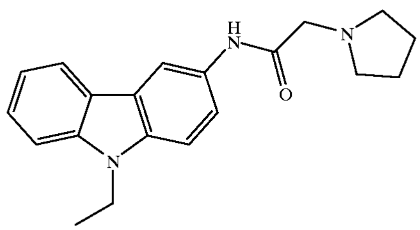 | N-(9-Ethyl-9H-carbazol-3-yl)-2-pyrrolidin-1-yl-acetamide | 322 |
| 25 | 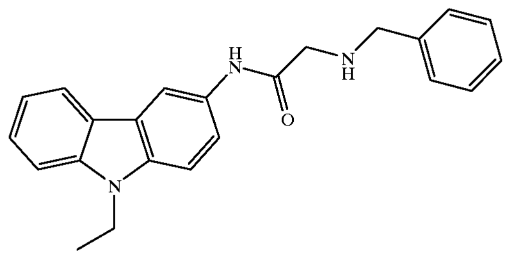 | 2-Benzylamino-N-(9-ethyl-9H-carbazol-3-yl)-acetamide | 358 |
| 26 | 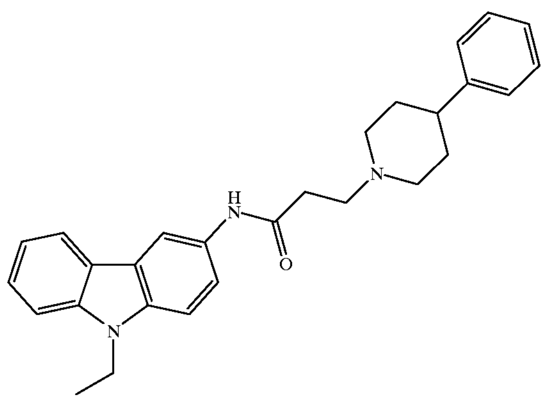 | N-(9-Ethyl-9H-carbazol-3-yl)-3-(4-phenyl-piperidin-1-yl)-propionamide | 426 |
| 27 | 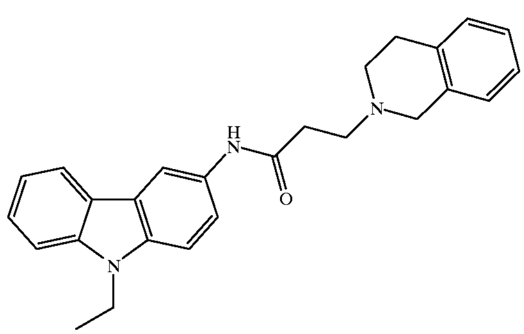 | 3-(3,4-Dihydro-1H-isoquinolin-2-yl)-N-(9-ethyl-9H-carbazol-3-yl)-propionamide | 398 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 28 | 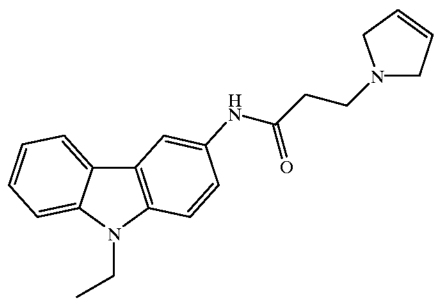 | 3-(2,5-Dihydro-pyrrol-1-yl)-N-(9-ethyl-9H-carbazol-3-yl)-propionamide | 334 |
| 29 | 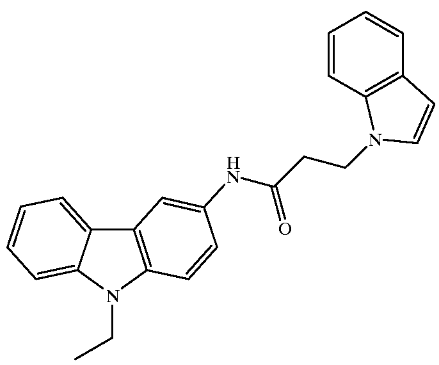 | N-(9-Ethyl-9H-carbazol-3-yl)-3-indol-1-yl-propionamide | 382 |
| 30 | 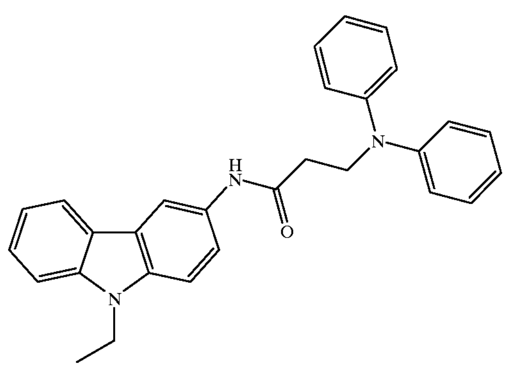 | 3-Diphenylamino-N-(9-ethyl-9H-carbazol-3-yl)-propionamide | 434 |
| 31 | 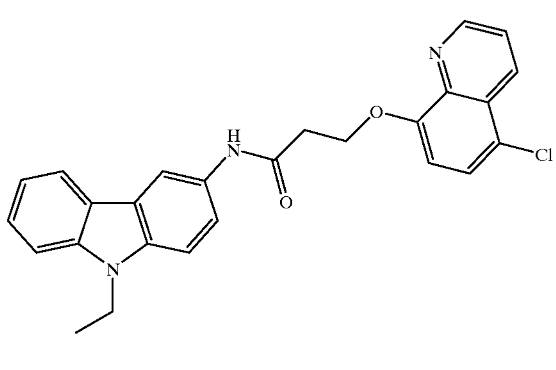 | 3-(5-Chloro-quinolin-8-yloxy)-N-(9-ethyl-9H-carbazol-3-yl)-propionamide | 444 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 32 | 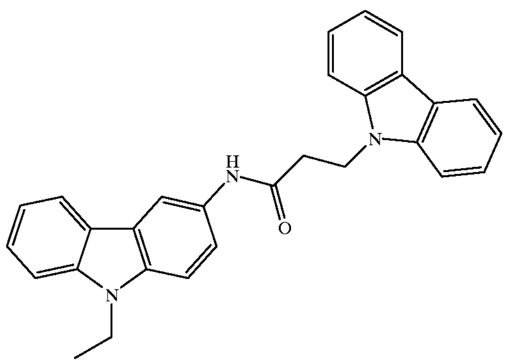 | 3-Carbazol-9-yl-N-(9-ethyl-9H-carbazol-3-yl)-propionamide | 432 |
| 33 | 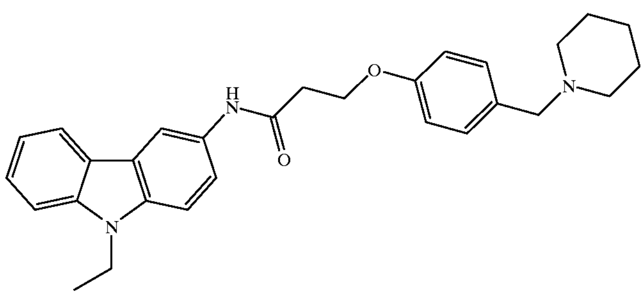 | N-(9-Ethyl-9H-carbazol-3-yl)-3-(4-piperidin-1-ylmethyl-phenoxy)-propionamide | 456 |
| 34 | 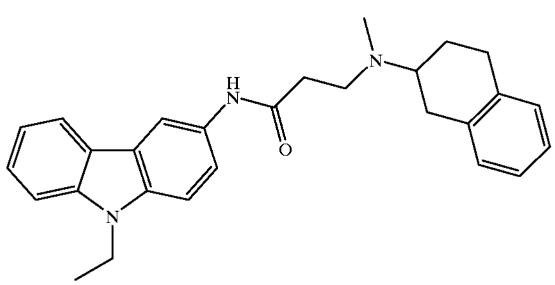 | N-(9-Ethyl-9H-carbazol-3-yl)-3-[methyl-(1,2,3,4-tetrahydro-naphthalen-2-yl)-amino]-propionamide | 426 |
| 35 | 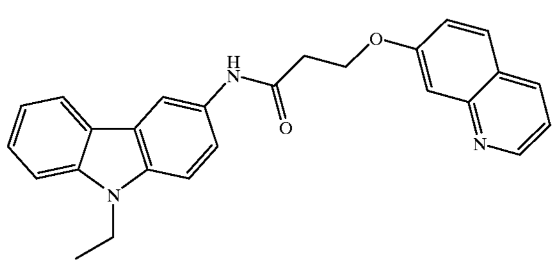 | N-(9-Ethyl-9H-carbazol-3-yl)-3-(quinolin-7-yloxy)-propionamide | 410 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 36 | 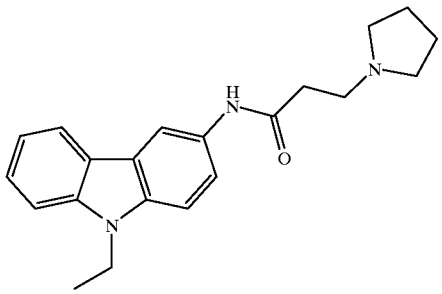 | N-(9-Ethyl-9H-carbazol-3-yl)-3-pyrrolidin-1-yl-propionamide | 336 |
| 37 | 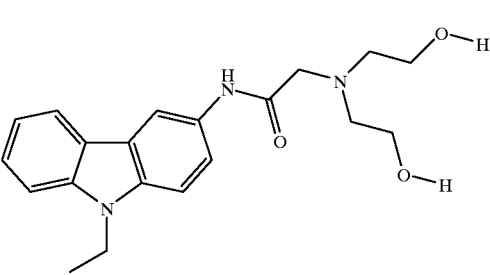 | 2-[Bis-(2-hydroxy-ethyl)-amino]-N-(9-ethyl-9H-carbazol-3-yl)-acetamide | 356 |
| 38 | 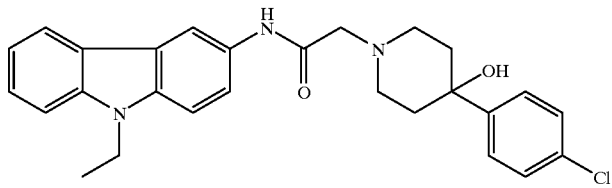 | 2-[4-(4-Chloro-phenyl)-4-hydroxy-piperidin-1-yl]-N-(9-ethyl-9H-carbazol-3-yl)-acetamide | 462 |
| 39 | 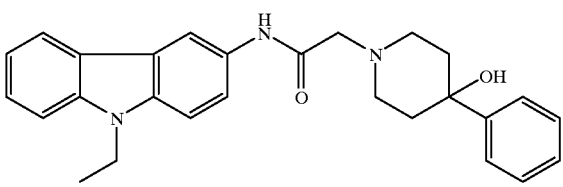 | N-(9-Ethyl-9H-carbazol-3-yl)-2-(4-hydroxy-4-phenyl-piperidin-1-yl)-acetamide | 428 |
| 40 | 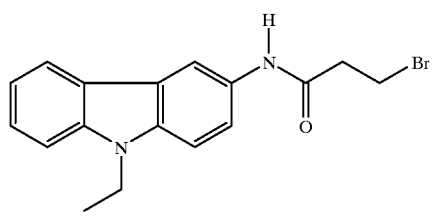 | 3-Bromo-N-(9-ethyl-9H-carbazol-3-yl)-propionamide | 345/347 |
| 41 | 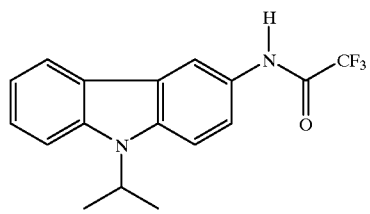 | N-(9-Isopropyl-9H-carbazol-3-yl)-trifluoroacetamide | 319[2] (M$^+$ − H) |

TABLE-continued

Carbazoles with Ki Values <1 uM NPY-5 Binding and Mass Spectrometry Data.

| Example | Structure | Name | Mass Spec Data m/z[1] |
|---|---|---|---|
| 42 | 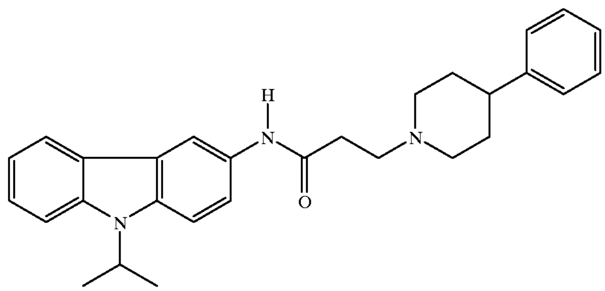 | N-(9-Isopropyl-9H-carbazol-3-yl)-3-(4-phenyl-piperidin-1-yl)-propionamide | 440 |
| 43 | 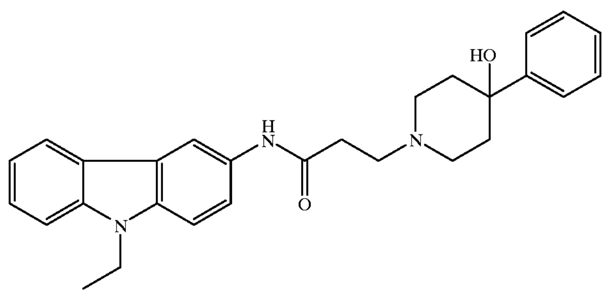 | N-(9-Ethyl-9H-carbazol-3-yl)-3-(4-hydroxy-4-phenyl-piperidin-1-yl)-propionamide | 442 |
| 44 | 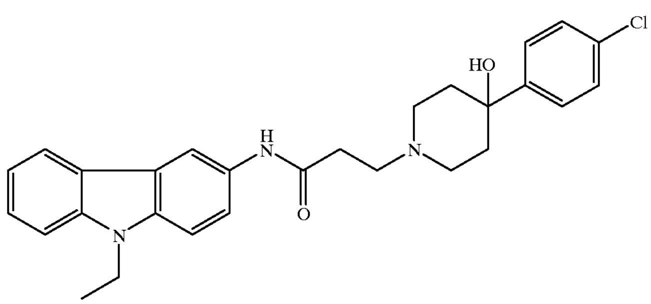 | 3-[4-(4-Chloro-phenyl)-4-hydroxy-piperidin-1-yl]-N-(9-ethyl-9H-carbazol-3-yl)-propionamide | 475[2] (M$^+$ − H) |
| 45 | 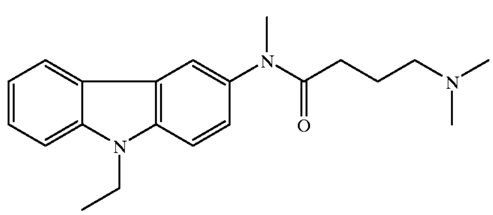 | 4-Dimethylamino-N-(9-ethyl-9H-carbazol-3-yl)-N-methyl-butyramide | 338 |
| 46 | 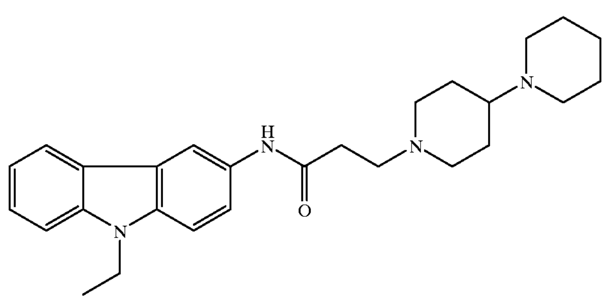 | 3-[1,4']Bipiperidinyl-1'-yl-N-(9-ethyl-9H-carbazol-3-yl)-propionamide | 433 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 47 | 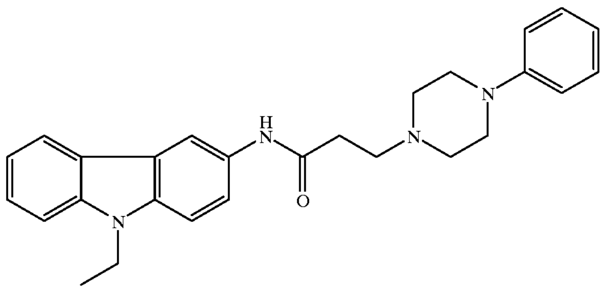 | N-(9-Ethyl-9H-carbazol-3-yl)-3-(4-phenyl-piperazin-1-yl)-propionamide | 427 |
| 48 | 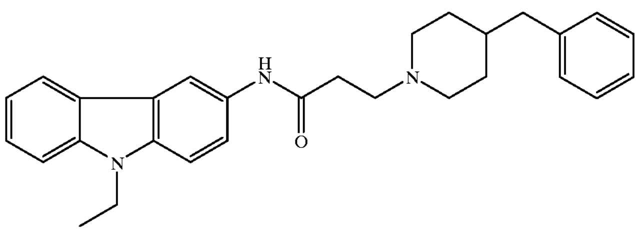 | 3-(4-Benzyl-piperidin-1-yl)-N-(9-ethyl-9H-carbazol-3-yl)-propionamide | 440 |
| 49 | 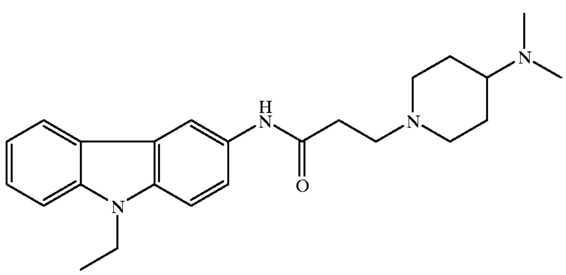 | 3-(4-Dimethylamino-piperidin-1-yl)-N-(9-ethyl-9H-carbazol-3-yl)-propionamide | 393 |
| 50 | 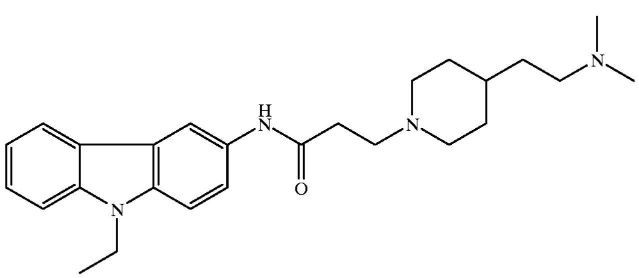 | 3-(4-Dimethylaminoethyl-piperidin-1-yl)-N-(9-ethyl-9H-carbazol-3-yl)-propionamide | 421 |
| 51 | 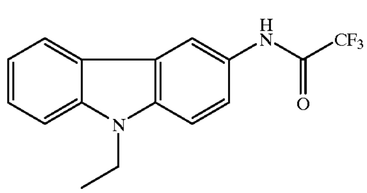 | N-(9-Methyl-9H-carbazol-3-yl)-trifluoroacetamide | 291[2] (M+ − H) |

TABLE-continued

Carbazoles with Ki Values <1 uM NPY-5 Binding and Mass Spectrometry Data.

| Example | Structure | Name | Mass Spec Data m/z[1] |
|---|---|---|---|
| 52 | 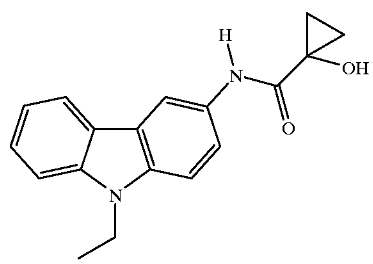 | 1-Hydroxy-cyclopropanecarboxylic acid (9-ethyl-9H-carbazol-3-yl)-amide | 295 |
| 53 | 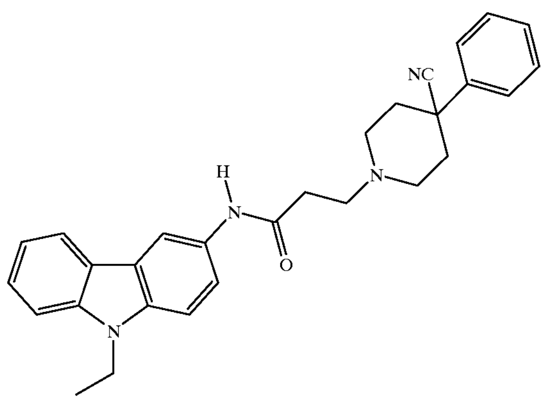 | N-(9-Ethyl-9H-carbazol-3-yl)-3-(4-cyano-4-phenyl-piperidin-1-yl)-propionamide | 451 |
| 54 | 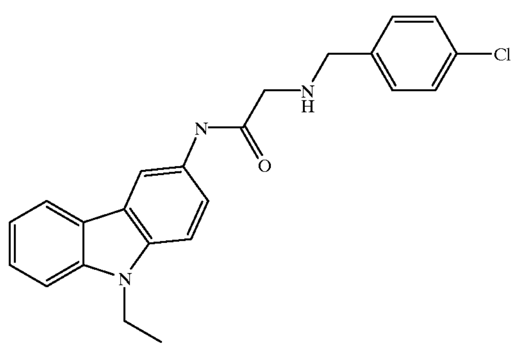 | 2-(4-Chloro)-benzylamino-N-(9-ethyl-9H-carbazol-3-yl)-acetamide | 392 |
| 55 | 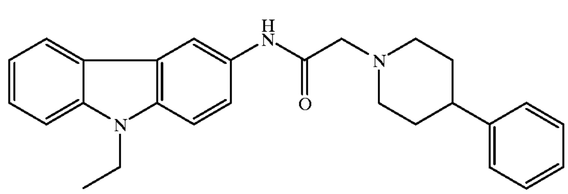 | N-(9-Ethyl-9H-carbazol-3-yl)-2-(4-phenyl-piperidin-1-yl)-acetamide | 412 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 56 | 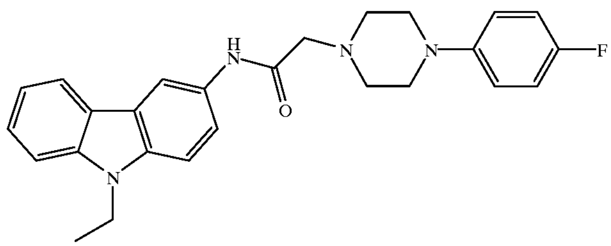 | N-(9-Ethyl-9H-carbazol-3-yl)-2-(4-(4-fluoro)-phenyl-piperazin-1-yl)-acetamide | 431 |
| 57 | 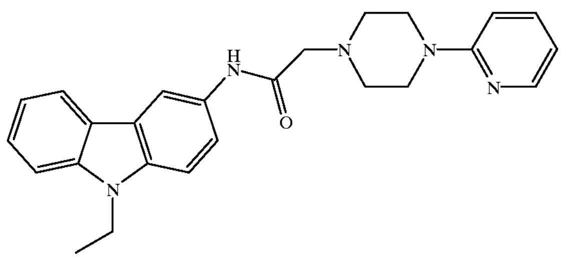 | N-(9-Ethyl-9H-carbazol-3-yl)-3-(4-pyridin-2-yl-piperazin-1-yl)-acetamide | 414 |
| 58 | 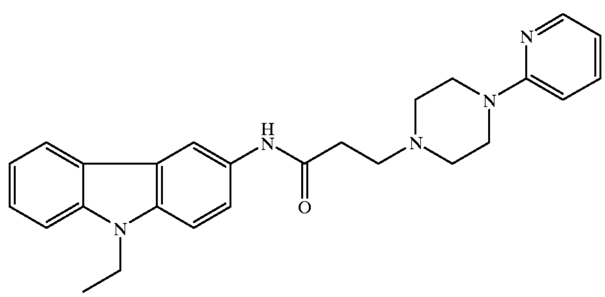 | N-(9-Ethyl-9H-carbazol-3-yl)-3-(4-pyridin-2-yl-piperazin-1-yl)-propionamide | 428 |
| 59 | 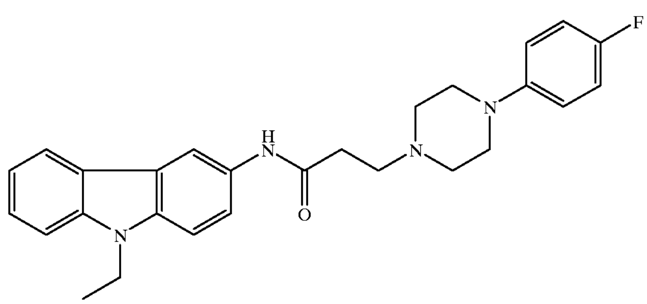 | N-(9-Ethyl-9H-carbazol-3-yl)-3-(4-(4-fluoro)-phenyl-piperazin-1-yl)-propionamide | 445 |
| 60 | 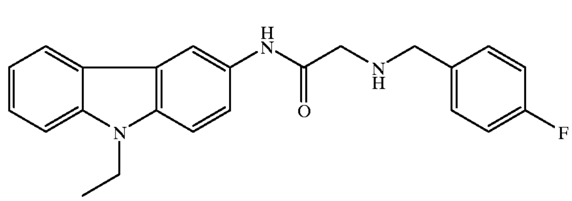 | 2-(4-fluoro)-benzylamino-N-(9-ethyl-9H-carbazol-3-yl)-acetamide | 376 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 61 | 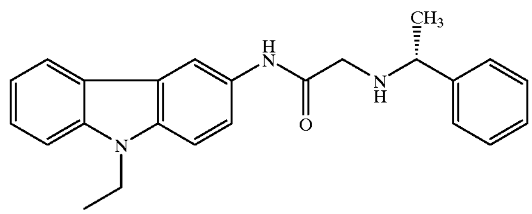 | (R)-N-(9-Ethyl-9H-carbazol-3-yl)-2-(1-phenyl-ethylamino)-acetamide | 372 |
| 62 | 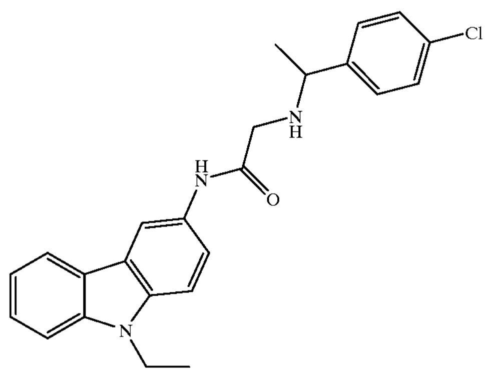 | (R)-N-(9-Ethyl-9H-carbazol-3-yl)-2-(1-(4-chloro)-phenyl-ethylamino)-acetamide | 406 |
| 63 | 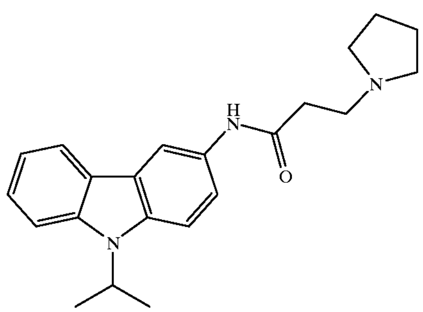 | N-(9-isopropyl-9H-carbazol-3-yl)-3-pyrrolidin-1-yl-propionamide | 350 |
| 64 | 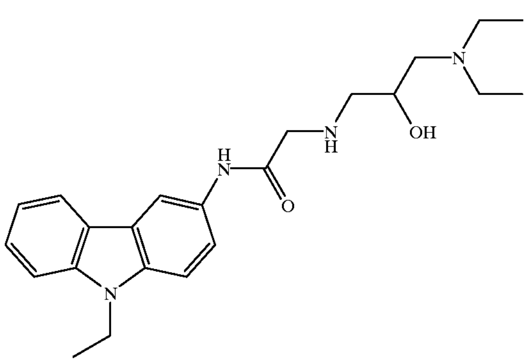 | 2-(3-Diethylamino-2-hydroxy-propyl-amino)-N-(9-ethyl-9H-carbazol-3-yl)-acetamide | 397 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 65 | 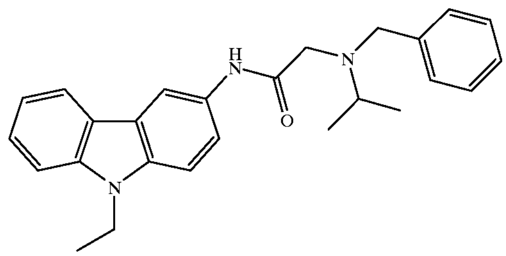 | 2-(Benzyl-isopropyl-amino)-N-(9-ethyl-9H-carbazol-3-yl)-acetamide | 400 |
| 66 | 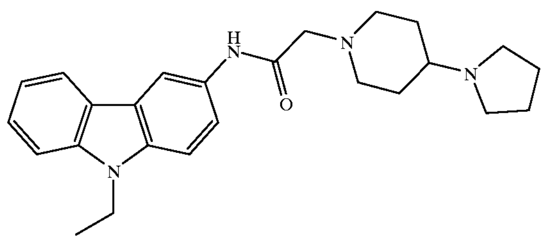 | N-(9-Ethyl-9H-carbazol-3-yl)-2-(4-pyrrolidin-1-yl-piperidin-1-yl)-acetamide | 405 |
| 67 | 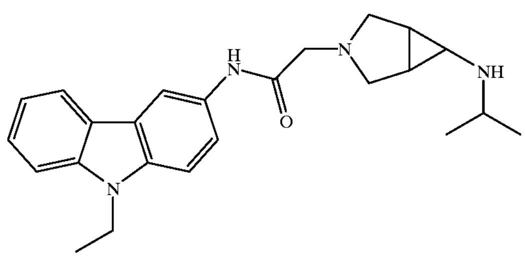 | N-(9-Ethyl-9H-carbazol-3-yl)-2-(6-isopropylamino-3-aza-bicyclo[3.1.0]hex-3-yl)-acetamide | 391 |
| 68 | 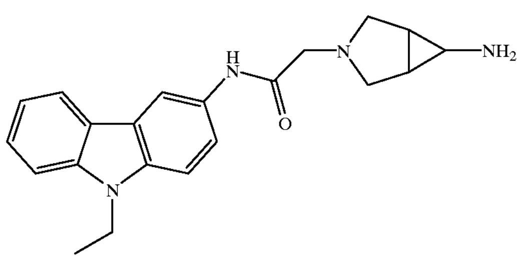 | N-(9-Ethyl-9H-carbazol-3-yl)-2-(6-amino-3-aza-bicyclo[3.1.0]hex-3-yl)-acetamide | 349 |
| 69 | 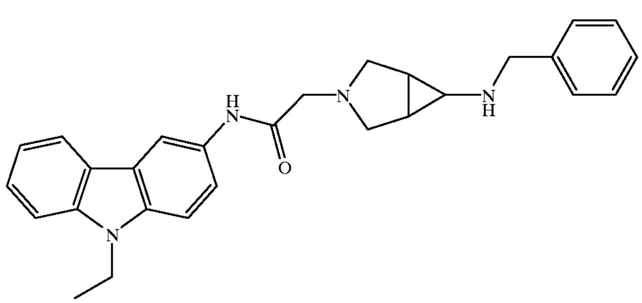 | N-(9-Ethyl-9H-carbazol-3-yl)-2-(6-benzylamino-3-aza-bicyclo[3.1.0]hex-3-yl)-acetamide | characterized by $^1$H-NMR |

TABLE-continued

Carbazoles with Ki Values <1 uM NPY-5 Binding and Mass Spectrometry Data.

| Example | Structure | Name | Mass Spec Data m/z[1] |
|---|---|---|---|
| 70 | 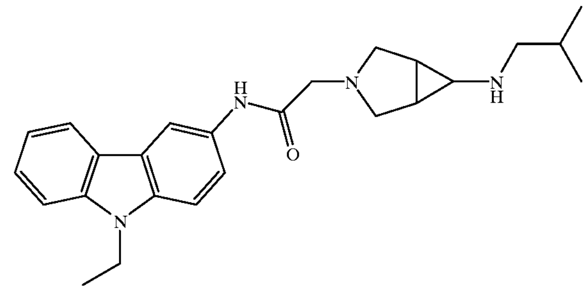 | N-(9-Ethyl-9H-carbazol-3-yl)-2-(6-isobutylamino-3-aza-bicyclo[3.1.0]hex-3-yl)-acetamide | 405 |
| 71 | 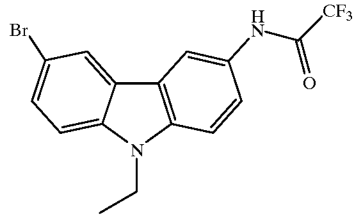 | N-3-Bromo-(9-ethyl-9H-carbazol-6-yl)-trifluoroacetamide | 383/385[2] (M[+] − H) |
| 72 | 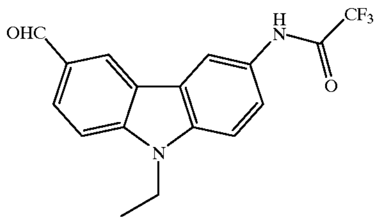 | N-(9-Ethyl-6-formyl-9H-carbazol-3-yl)-trifluoroacetamide | 333[2] (M[+] − H) |
| 73 | 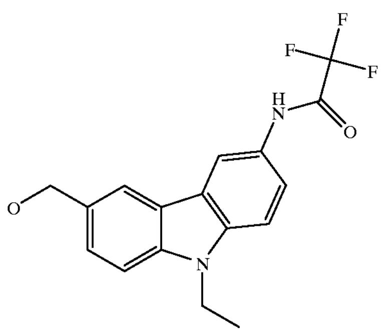 | N-(9-Ethyl-6-hydroxymethyl-9H-carbazol-3-yl)-trifluoroacetamide | 337 |
| 74 | 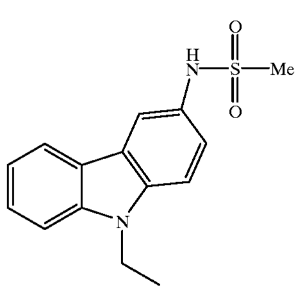 | N-(9-Ethyl-9H-carbazol-3-yl)-methanesulfonamide | 279[2] (M[+] − H) |

TABLE-continued

Carbazoles with Ki Values <1 uM NPY-5 Binding and Mass Spectrometry Data.

| Example | Structure | Name | Mass Spec Data m/z[1] |
|---|---|---|---|
| 75 | 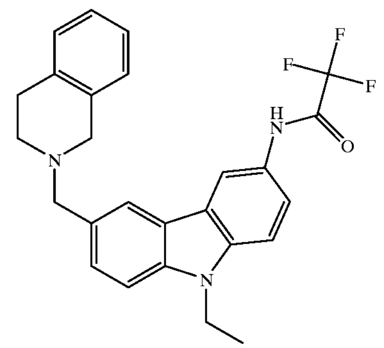 | N-[6-(3,4-Dihydro-1H-isoquinolin-2-ylmethyl)-9-ethyl-9H-carbazol-3-yl]-2,2,2-trifluoro-acetamide | 488 |
| 76 | 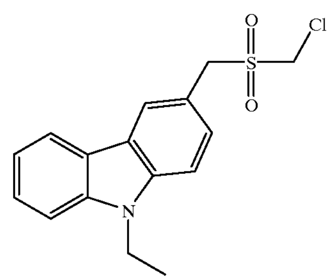 | N-(9-Ethyl-9H-carbazol-3-yl)-chloromethanesulfonamide | 321[2] (M$^+$ − H) |
| 77 | 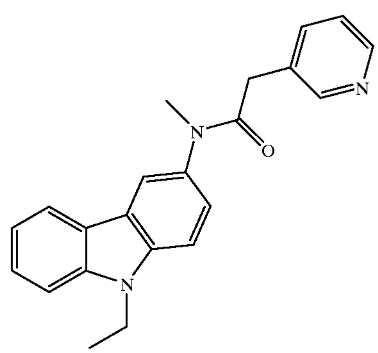 | N-(9-Ethyl-9H-carbazol-3-yl)-2-pyridin-3-yl-N-methylacetamide | 344 |
| 78 | 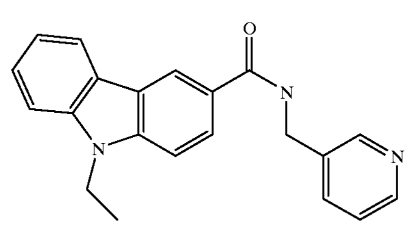 | 9-Ethyl-9H-carbazole-3-carboxylic acid (pyridin-3-ylmethyl)-amide | 330 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 79 | 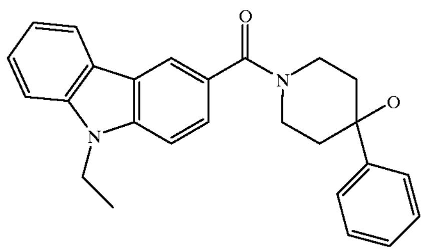 | (9-Ethyl-9H-carbazol-3-yl)-(4-hydroxy-4-phenyl-piperidin-1-yl)-methanone | 399 |
| 80 | 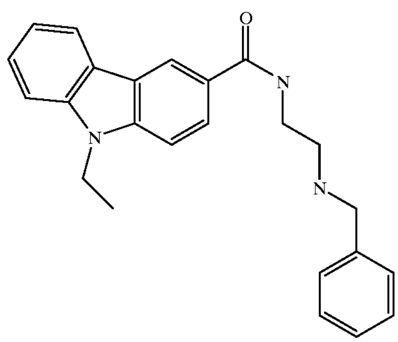 | 9-Ethyl-9H-carbazole-3-carboxylic acid (2-benzylamino-ethyl)-amide | 372 |
| 81 | 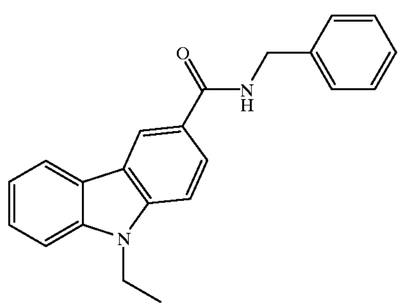 | 9-Ethyl-9H-carbazole-3-carboxylic acid benzylamide | 329 |
| 82 | 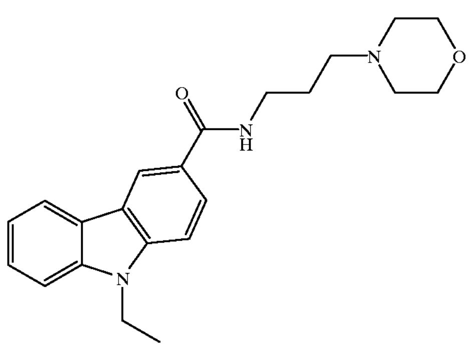 | 9-Ethyl-9H-carbazole-3-carboxylic acid (3-morpholin-4-yl-propyl)-amide | 366 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 83 | 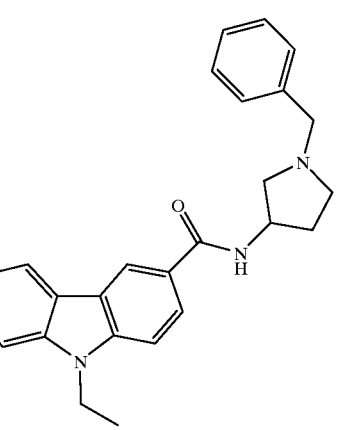 | 9-Ethyl-9H-carbazole-3-carboxylic acid (1-benzyl-pyrrolidin-3-yl)-amide | 398 |
| 84 | 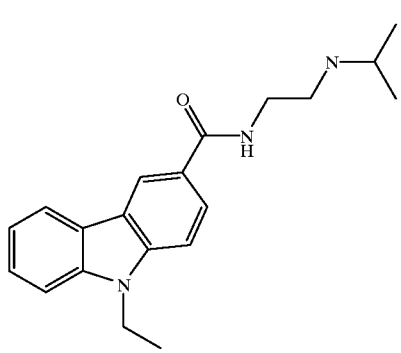 | 9-Ethyl-9H-carbazole-3-carboxylic acid (2-isopropylamino-ethyl)-amide | 324 |
| 85 | 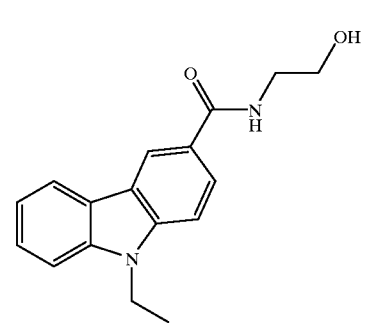 | 9-Ethyl-9H-carbazole-3-carboxylic acid (2-hydroxy-ethyl)-amide | 283 |
| 86 | 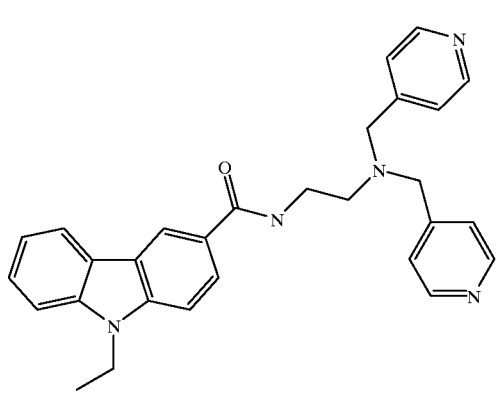 | 9-Ethyl-9H-carbazole-3-carboxylic acid [2-(bis-pyridin-4-ylmethyl-amino)-ethyl]-amide | 464 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 87 | 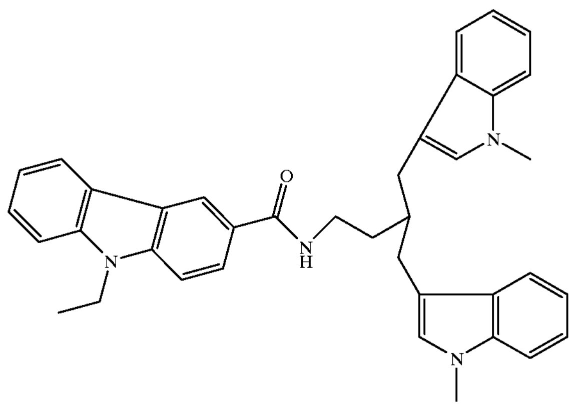 | 9-Ethyl-9H-carbazole-3-carboxylic acid {2-[bis-(1-methyl-1H-indol-3-ylmethyl)-amino]-ethyl}-amide | 568 |
| 88 | 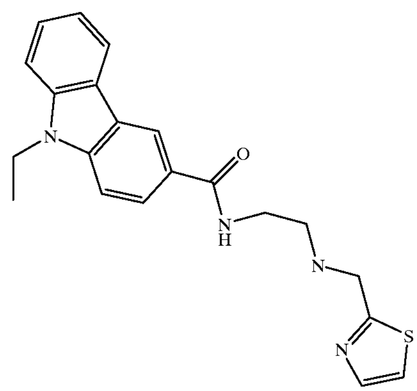 | 9-Ethyl-9H-carbazole-3-carboxylic acid {2-[(thiazol-2-ylmethyl)-amino]-ethyl}-amide | 379 |
| 89 | 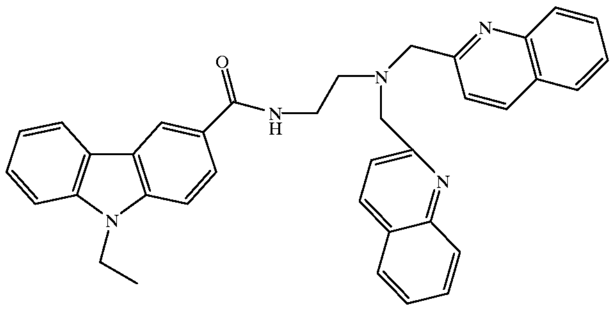 | 9-Ethyl-9H-carbazole-3-carboxylic acid [2-(bis-quinolin-2-ylmethyl-amino)-ethyl]-amide | 564 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 90 | 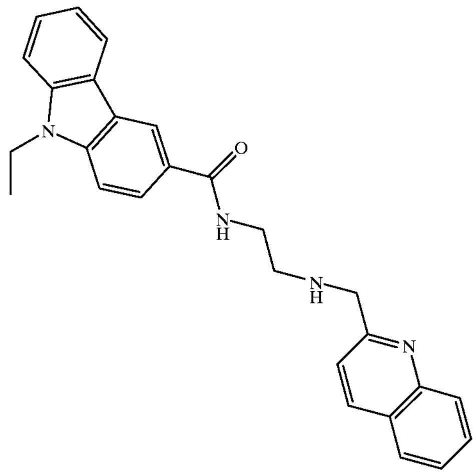 | 9-Ethyl-9H-carbazole-3-carboxylic acid {2-[(quinolin-2-ylmethyl)-amino]-ethyl}-amide | 423 |
| 91 | 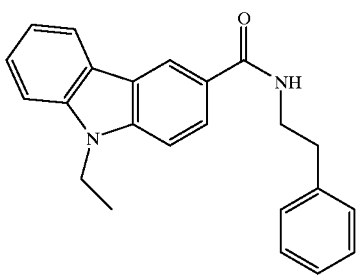 | 9-Ethyl-9H-carbazole-3-carboxylic acid phenethyl-amide | 343 |
| 92 | 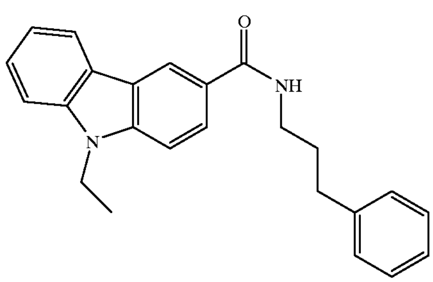 | 9-Ethyl-9H-carbazole-3-carboxylic acid (3-phenyl-propyl)-amide | 357 |
| 93 | 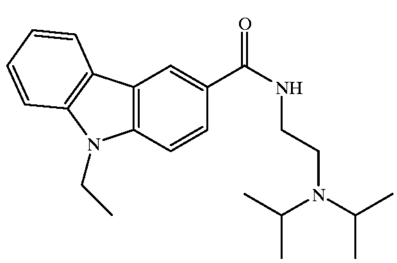 | 9-Ethyl-9H-carbazole-3-carboxylic acid (2-diisopropylamino-ethyl)-amide | 366 |

TABLE-continued

Carbazoles with Ki Values <1 uM NPY-5 Binding and Mass Spectrometry Data.

| Example | Structure | Name | Mass Spec Data m/z[1] |
|---|---|---|---|
| 94 | 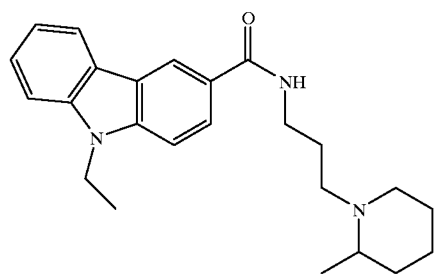 | 9-Ethyl-9H-carbazole-3-carboxylic acid [3-(2-methyl-piperidin-1-yl)-propyl]-amide | 378 |
| 95 | 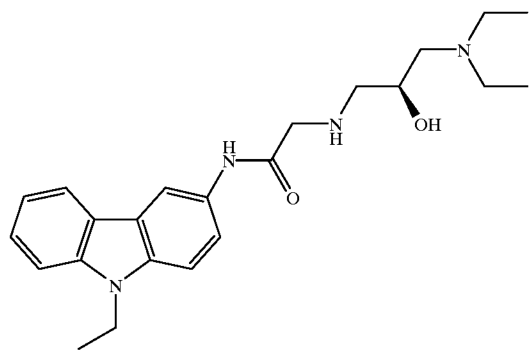 | (S)-2-(3-Diethylamino-2-hydroxy-propylamino)-N-(9-ethyl-9H-carbazol-3-yl)-acetamide | 397 |
| 96 | 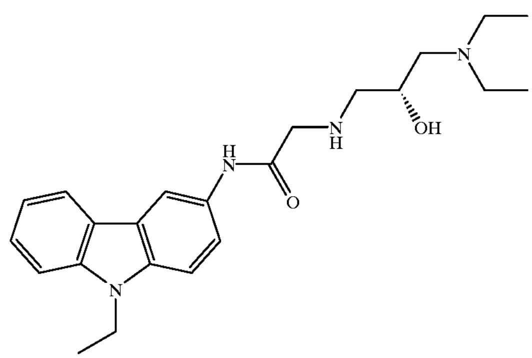 | (R)-2-(3-Diethylamino-2-hydroxy-propylamino)-N-(9-ethyl-9H-carbazol-3-yl)-acetamide | 397 |
| 97 | 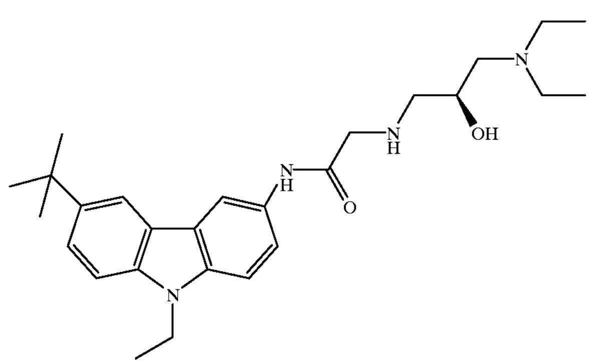 | (S)-N-(6-tert-Butyl-9-ethyl-9H-carbazol-3-yl)-2-(3-diethylamino-2-hydroxy-propylamino)-acetamide | 453 |

[1]All mass spectrometry data obtained on a Fisons VG Platform II mass spectrometer. All m/z values are (M$^+$ + H) obtained by using APcl+ unless otherwise indicated.
[2]Mass spectrometry data obtained from the above instrument using APcl–.

What is claimed is:

1. A compound of formula

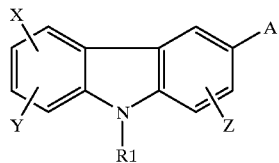

I wherein X, Y, and Z are independently selected from
(a) hydrogen;
(b) halogen;
(c) hydroxy;
(d) nitro;
(e) cyano;
(f) $C_1$–$C_6$ alkyl;
(g) $C_1$–$C_6$ alkoxy;
(h) —$NR^7R^8$;
(i) —$CH_2NR^7R^8$;
(j) —$CH_2OR^7$;
(k) —$C(O)NR^7R^8$;
(l) $C_1$–$C_6$ alkylaryl; and $R^1$ is $C_1$–$C_5$ alkyl, alkylaryl, alkenyl, (cycloalkyl)alkyl, or mono or $C_1$–$C_6$ polyfluoroalkyl;

and A is $NR^2COR^3$ or $NR^2SO_2R^3$ wherein;

$R^2$ is hydrogen, $C_1$–$C_3$ alkyl, $C_1$–$C_3$ alkylaryl, $C_1$–$C_3$ alkenyl, $C_2$–$C_4$ alkynyl, or $C_1$–$C_3$ polyfluoroalkyl;

$R^3$ is selected from $C_1$–$C_6$ mono or polyfluoroalkyl, $C_1$–$C_6$ alkyl, excluding $CH_3$, $C_3$–$C_8$ cycloalkyl, $C_2$–$C_6$ alkenyl, $C_5$–$C_8$ cycloalkenyl, $C_2$–$C_6$ alkynyl, or $C_4$–$C_8$ cycloazaalkyl; wherein $C_1$–$C_6$ alkyl, $C_3$–$C_8$ cycloalkyl, $C_2$–$C_6$ alkenyl, $C_5$–$C_8$ cycloalkenyl, $C_2$–$C_6$ alkynyl, or $C_4$–$C_8$ cycloazaalkyl can be independently substituted with one to three substituents selected from the group consisting of F, Br, Cl, aryl, aryloxy, $NR_4R_5$, ($C_1$–$C_6$) alkoxy, $NO_2$, OH, ON, COOH, and $C_1$–$C_6$ alkylthio, $R^4$ and $R^5$ are selected independently from H, $C_1$–$C_6$ alkyl, $C_2$–$C_6$ alkenyl, $C_3$–$C_6$ cycloalkyl, $C_5$–$C_8$ cycloalkenyl, $C_2$–$C_6$ alkynyl, aryl, alkylaryl, $R^7$ and $R^8$ are independently selected from $C_1$–$C_6$ alkyl; $C_2$–$C_6$ alkenyl; $C_2$–$C_6$ alkynyl or aryl and optical and geometric or tautomeric isomers thereof; and nontoxic pharmacologically acceptable acid addition salts, N-oxides, esters, and quaternary ammonium salts thereof, with provisos that:

when X, Y and Z are hydrogen and A is $NR^2SO_2R^3$, wherein $R^2$ is hydrogen and $R^3$ is perfluoroalkyl, $R^1$ is not $C_1$–$C_5$ alkyl; and when only one of either X or Y is —$CH_2OR^7$, then A is not acylamido.

2. A compound of claim 1 which is of the formula

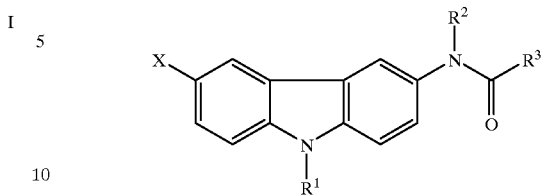

II where
X is selected from hydrogen; halogen; alkoxy; $NR^7R^8$; —$CH_2NR^7R^8$; —$CH_2OR^7$; and —$C(O)NR^7R^8$;

$R^1$ is $C_1$–$C_5$ alkyl, alkenyl, alkylaryl, (cycloalkyl)alkyl, or mono or polyfluoroalkyl;

$R^2$ is hydrogen or $C_1$–$C_3$ alkyl;

$R^3$ is selected from $CF_3$; mono or polyfluoroalkyl, heteroaryl, $C_1$–$C_6$ alkyl, excluding $CH_3$, $C_3$–$C_8$ cycloalkyl, $C_2$–$C_6$ alkenyl, $C_5$–$C_8$ cycloalkenyl, $C_2$–$C_6$ alkynyl, or $C_4$–$C_8$ cycloazaalkyl; wherein $C_1$–$C_6$ alkyl, $C_3$–$C_8$ cycloalkyl, $C_2$–$C_6$ alkenyl, $C_5$–$C_8$ cycloalkenyl, $C_2$–$C_6$ alkynyl, or $C_4$–$C_8$ cycloazaalkyl can be independently substituted with one to three substituents selected from the group consisting of F, Br, Cl, aryl, heteroaryl, aryloxy, heteroaryloxy, $NR^4R^5$, ($C_1$–$C_6$) alkoxy, $NO_2$, OH, CN, COOH, and thioalkyl.

3. A compound of claim 2 wherein X is hydrogen or halogen; $R^1$ is methyl, ethyl, propyl, cyclopropylmethyl, or isopropyl; $R^2$ is hydrogen, and $R^3$ is selected from $C_1$–$C_3$ alkyl which can be independently substituted with one to two substituents selected from the group consisting of aryl, $NR^4R^5$, ($C_1$–$C_6$)alkoxy, aryloxy, and OH.

4. A compound of claim 3 wherein X is hydrogen, $R^1$ is ethyl, $R^2$ is hydrogen and $R^3$ is methyl or ethyl substituted with phenyl, halogen substituted phenyl, or —$NR^4R^5$.

5. A compound of claim 4 wherein —$NR^4R^5$ is dimethyl amino, diethyl amino, or (R)-, (S)-, or a mixture of (R)- and (S)-3-diethylamino-2-hydroxypropylamino.

6. A compound of claim 1 which is of the formula

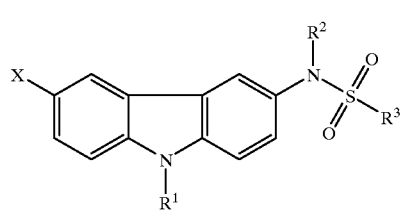

IV where
X is selected from hydrogen; halogen; alkoxy; $NR^7R^8$; —$CH_2NR^7R^8$; —$CH_2OR^7$; and —$C(O)NR^7R^8$;

$R^1$ is $C_1$–$C_5$ alkyl, alkenyl, alkylaryl or (cycloalkyl)alkyl;

$R^2$ is hydrogen or $C_1$–$C_3$ alkyl;

$R^3$ is selected from $CF_3$; mono or polyfluoroalkyl, $C_1$–$C_6$ alkyl (excluding $CH_3$), $C_3$–$C_8$ cycloalkyl, $C_2$–$C_6$ alkenyl, $C_5$–$C_8$ cycloalkenyl, $C_2$–$C_6$ alkynyl, or $C_4$–$C_8$ cycloazaalkyl; wherein $C_1$–$C_6$ alkyl, $C_3$–$C_8$ cycloalkyl, $C_2$–$C_6$ alkenyl, $C_5$–$C_8$ cycloalkenyl, $C_2$–$C_6$ alkynyl, or $C_4$–$C_8$ cycloazaalkyl can be independently substituted with one to three substituents selected from the group consisting of F, Br, Cl, aryl, aryloxy, $NR^4R^5$, ($C_1$–$C_6$) alkoxy, $NO_2$, OH, CN, COOH, and $C_1$–$C_6$ thioalkyl.

7. A compound of claim 6 wherein X is hydrogen or bromine, $R^1$ is methyl, ethyl, or isopropyl; $R^2$ is hydrogen, and $R^3$ is selected from $C_1$–$C_5$ alkyl which can be independently substituted with one to two substituents selected from the group consisting of aryl, aryloxy, $NR^4R^5$, ($C_1$–$C_6$) alkoxy, and OH.

8. A pharmaceutical composition for treating obesity comprising a compound of claim 1 and a pharmaceutically acceptable carrier.

9. A method for treating obesity comprising administering to a mammal requiring such treatment an amount of a compound according to claim 1 effective in treating said disorder.

10. A pharmaceutical composition for treating disorders arising from neuropeptide Y neurotransmission comprising an amount of a compound of claim 1 effective in treating said disorder and a pharmaceutically acceptable carrier.

11. A method for treating disorders arising from neuropeptide Y neurotransmission comprising administering to a mammal requiring such treatment an amount of a compound of claim 1 effective in treating said disorder.

12. A compound of claim 1 selected from the group consisting of:
2-Dimethylamino-N-(9-ethyl-9H-carbazol-3-yl)-acetamide;
3-Diethylamino-N-(9-ethyl-9H-carbazol-3-yl)-propionamide;
N-(9-Ethyl-9H-carbazol-3-yl)-2-fluoro-benzamide;
4-Dimethylamino-N-(9-ethyl-9H-carbazol-3-yl)-butyramide;
N-(9-Ethyl-9H-carbazol-3-yl)-2-hydroxy-2,2-diphenyl-acetamide;
N-(9-Ethyl-9H-carbazol-3-yl)-2-hydroxy-2-methyl-propionamide;
N-(9-Ethyl-9H-carbazol-3-yl)-2-hydroxy-2-methyl-butyramide;
N-(9-Ethyl-9H-carbazol-3-yl)-2-hydroxy-2-phenyl-propionamide;
(R)-N-(9-Ethyl-9H-carbazol-3-yl)-2-hydroxy-2-phenyl-propionamide;
2-Bromo-N-(9-ethyl-9H-carbazol-3-yl)-acetamide; and
3-Dimethylamino-N-(9-ethyl-9H-carbazol-3-yl)-propionamide.

13. A compound of claim 1 selected from the group consisting of:
2-[Bis-(2-hydroxy-ethyl)-amino]-N-(9-ethyl-9H-carbazol-3-yl)-acetamide;
2-Benzylamino-N-(9-ethyl-9H-carbazol-3-yl)-acetamide;
3-Diphenylamino-N-(9-ethyl-9H-carbazol-3-yl)-propionamide; and
N-(9-Ethyl-9H-carbazol-3-yl)-3-(4-piperidin-1-ylmethyl-phenoxy)-propionamide;
N-(9-Ethyl-9H-carbazol-3-yl)-3-[methyl-(1,2,3,4-tetrahydro-naphthalen-2-yl)-amino]-propionamide;
N-(9-Ethyl-9H-carbazol-3-yl)-3-(quinolin-7-yloxy)-propionamide; and
2-[Bis-(2-hydroxy-ethyl)-amino]-N-(9-ethyl-9H-carbazol-3-yl)-acetamide.

14. A compound of claim 1 selected from the group consisting of:
3-Bromo-N-(9-ethyl-9H-carbazol-3-yl)-propionamide;
N-(9-Isopropyl-9H-carbazol-3-yl)-trifluoroacetamide;
4-Dimethylamino-N-(9-ethyl-9H-carbazol-3-yl)-N-methyl-butyramide;
N-(9-Methyl-9H-carbazol-3-yl)-trifluoroacetamide;
1-Hydroxy-cyclopropanecarboxylic acid (9-ethyl-9H-carbazol-3-yl)-amide; and
2-(4-Chloro)-benzylamino-N-(9-ethyl-9H-carbazol-3-yl)-acetamide.

15. A compound of claim 1 selected from the group consisting of:
2-(4-fluoro)-benzylamino-N-(9-ethyl-9H-carbazol-3-yl)-acetamide;
(R)-N-(9-Ethyl-9H-carbazol-3-yl)-2-(1-phenyl-ethylamino)-acetamide;
(R)-N-(9-Ethyl-9H-carbazol-3-yl)-2-(1-(4-chloro)-phenyl-ethylamino)-acetamide;
2-(3-Diethylamino-2-hydroxy-propylamino)-N-(9-ethyl-9H-carbazol-3-yl)-acetamide;
2-(Benzyl-isopropyl-amino)-N-(9-ethyl-9H-carbazol-3-yl)-acetamide;
N-3-Bromo-(9-ethyl-9H-carbazol-6-yl)-trifluoroacetamide;
N-(9-Ethyl-6-formyl-9H-carbazol-3-yl)-trifluoroacetamide;
N-(9-Ethyl-6-hydroxymethyl-9H-carbazol-3-yl)-trifluoroacetamide;
N-(9-Ethyl-9H-carbazol-3-yl)-methanesulfonamide;
N-(9-Ethyl-9H-carbazol-3-yl)-chloromethanesulfonamide;
2-Bromo-N-(9-ethyl-9H-carbazol-3-yl)-acetamide; and
3-Dimethylamino-N-(9-ethyl-9H-carbazol-3-yl)-propionamide.

16. A compound of claim 1 selected from the group consisting of:
2-[Bis-(2-hydroxy-ethyl)-amino]-N-(9-ethyl-9H-carbazol-3-yl)-acetamide;
2-Benzylamino-N-(9-ethyl-9H-carbazol-3-yl)-acetamide;
3-Diphenylamino-N-(9-ethyl-9H-carbazol-3-yl)-propionamide;
N-(9-Ethyl-9H-carbazol-3-yl)-3-(4-piperidin-1-ylmethyl-phenoxy)-propionamide;
N-(9-Ethyl-9H-carbazol-3-yl)-3-[methyl-(1,2,3,4-tetrahydro-naphthalen-2-yl)-amino]-propionamide;
N-(9-Ethyl-9H-carbazol-3-yl)-3-(quinolin-7-yloxy)-propionamide;
2-[Bis-(2-hydroxy-ethyl)-amino]-N-(9-ethyl-9H-carbazol-3-yl)-acetamide;
3-Bromo-N-(9-ethyl-9H-carbazol-3-yl)-propionamide; and
N-(9-Isopropyl-9H-carbazol-3-yl)-acetamide.

17. A compound of claim 1 selected from the group consisting of:
4-Dimethylamino-N-(9-ethyl-9H-carbazol-3-yl)-N-methyl-butyramide;
N-(9-Methyl-9H-carbazol-3-yl)-trifluoroacetamide;
1-Hydroxy-cyclopropanecarboxylic acid (9-ethyl-9H-carbazol-3-yl)-amide;
2-(4-Chloro)-benzylamino-N-(9-ethyl-9H-carbazol-3-yl)-acetamide; and
2-(4-fluoro)-benzylamino-N-(9-ethyl-9H-carbazol-3-yl)-acetamide.

18. A compound of claim 1 selected from the group consisting of:
(R)-N-(9-Ethyl-9H-carbazol-3-yl)-2-(1-phenyl-ethylamino)-acetamide;
(R)-N-(9-Ethyl-9H-carbazol-3-yl)-2-(1-(4-chloro)-phenyl-ethylamino)-acetamide;
(R)-, (S)- or a mixture of (R)- and (S)-2-(3-Diethylamino-2-hydroxy-propylamino)-N-(9-ethyl-9H-carbazol-3-yl)-acetamide;
(S)-N-(6-tert-Butyl-9-ethyl-9H-carbazol-3-yl)-2-(3-diethylamino-2-hydroxy-propylamino)-acetamide,
2-(Benzyl-isopropyl-amino)-N-(9-ethyl-9H-carbazol-3-yl)-acetamide;
N-3-Bromo-(9-ethyl-9H-carbazol-6-yl)-trifluoroacetamide;
N-(9-Ethyl-6-formyl-9H-carbazol-3-yl)-trifluoroacetamide; and
N-(9-Ethyl-6-hydroxymethyl-9H-carbazol-3-yl)-trifluoroacetamide.

19. A compound of claim 1 selected from the group consisting of:

N-(9-Ethyl-9H-carbazol-3-yl)-methanesulfonamide; and
N-(9-Ethyl-9H-carbazol-3-yl)-chloromethanesulfonamide.

20. The method of claim 9 wherein said mammal is a dog or cat.

21. The method of claim 10 wherein said mammal is a dog or cat.

22. The method of claim 11 wherein said mammal is a dog or cat.

23. The method of claim 9 wherein said mammal is a human.

24. The method of claim 10 wherein said mammal is a human.

25. The method of claim 11 wherein said mammal is a human.

* * * * *